(12) United States Patent  
George et al.

(10) Patent No.: US 7,678,062 B2  
(45) Date of Patent: Mar. 16, 2010

(54) FLOW-INDEPENDENT PARAMETER ESTIMATION BASED ON TIDAL BREATHING EXHALATION PROFILES

(75) Inventors: Steven C. George, Irvine, CA (US); Peter Condorelli, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 734 days.

(21) Appl. No.: 11/599,684

(22) Filed: Nov. 14, 2006

(65) Prior Publication Data

US 2007/0167854 A1    Jul. 19, 2007

Related U.S. Application Data

(62) Division of application No. 10/358,802, filed on Feb. 5, 2003, now Pat. No. 7,156,813.

(60) Provisional application No. 60/354,781, filed on Feb. 5, 2002, provisional application No. 60/380,175, filed on May 13, 2002.

(51) Int. Cl.  
*A61B 5/00* (2006.01)

(52) U.S. Cl. ...................................................... 600/532

(58) Field of Classification Search .................... None  
See application file for complete search history.

(56) References Cited

U.S. PATENT DOCUMENTS

2002/0193698 A1* 12/2002 Moilanen et al. ............ 600/532

* cited by examiner

*Primary Examiner*—Robert L Nasser  
(74) *Attorney, Agent, or Firm*—Daniel L. Dawes; Marcus C. Dawes

(57) ABSTRACT

Parametric characterization of nitric oxide (NO) gas exchange using a two-compartment model of the lungs is a non-invasive technique to characterize inflammatory lung diseases. The technique applies the two-compartment model to parametric characterization of NO gas exchange from a tidal breathing pattern. The model is used to estimate up to six flow-independent parameters, and to study alternate breathing patterns.

11 Claims, 13 Drawing Sheets

| PARAMETER | UNITS | MEAN[a] | RANGE[b] | TIDAL BREATHS REQUIRED[c] | | | |
|---|---|---|---|---|---|---|---|
| | | | | +5% | +10% | +25% | +50% |
| UNFILTERED | | | | | | | |
| $D_{NO,air}$ | $ml \cdot s^{-1} \cdot ppb^{-1}$ | 1.3 | 0-10 | d | d | d | d |
| $J_{NO,max}$ | $ml \cdot s^{-1}$ | 600 | 580-610 | 2 | 1 | 1 | 1 |
| $D_{NO,alv}/V_{alv}$ | $s^{-1}$ | 1.0 | 0.8-1.2 | 120 | 35 | 9 | 4 |
| $C_{alv,ss}$ | ppb | 0.15 | 0-0.25 | 1,100 | 260 | 40 | 10 |
| KALMAN FILTERED | | | | | | | |
| $D_{NO,air}$ | $ml \cdot s^{-1} \cdot ppb^{-1}$ | 1.4 | 0-5 | 25,000 | 5,400 | 815 | 200 |
| $J_{NO,max}$ | $ml \cdot s^{-1}$ | 600 | 595-605 | 1 | 1 | 1 | 1 |
| $D_{NO,alv}/V_{alv}$ | $s^{-1}$ | 0.91 | 0.86-0.96 | 26 | 8 | 2 | 1 |
| $C_{alv,ss}$ | ppb | 0.10 | 0-0.16 | 1,200 | 250 | 30 | 9 |

FIG. 3

Central, lower and upper limits for flow-independent parameters.

| Parameter | Units | Lower Limit[a] | Central Value[a] | Upper Limit[a] |
|---|---|---|---|---|
| $D_{awNO}$ | $pl\text{-}s^{-1}\text{-}ppb^{-1}$ | 2.0 | 4.2 | 7.0 |
| $J'_{awNO}$ | $pl\text{-}s^{-1}$ | 500 | 640 | 800 |
| $\hat{D}_{alvNO}$ | $s^{-1}$ | 0.2 | 0.46 | 1.0 |
| $C_{alv,ss}$ | ppb | 1.5 | 2.5 | 3.5 |
| $V_{aw}$ | ml | 150 | 200 | 250 |
| $V_{ds}$ | ml | 50 | 75 | 100 |

[a] Central values, lower and upper limits based on best unbiased estimates (18) determined in previous work for single-breath maneuvers (4, 10, 26, 30, 31, 32, 34).

*FIG. 7*

FLOW-INDEPENDENT PARAMETER ESTIMATION BASED ON TIDAL BREATHING EXHALATION PROFILES

The application is a divisional of application Ser. No. 10/358,802, filed Feb. 5, 2003, now U.S. Pat. No. 7,156,813, which claims priority from U.S. provisional patent application Ser. No. 60/354,781 filed Feb. 5, 2002 and entitled FLOW-INDEPENDENT PARAMETER ESTIMATION BASED ON TIDAL BREATHING EXHALATION PROFILES, and U.S. provisional patent application Ser. No. 60/380,175 filed May 13, 2002 and entitled CHARACTERIZING NITRIC OXIDE EXCHANGE DYNAMICS DURING TIDAL BREATHING, both of which are incorporated herein by reference and to which priority is claimed pursuant to 5 USC 119.

BACKGROUND OF THE INVENTION

1. Field of the Invention

The invention relates to a method and apparatus for determining physiological parameters indicative of lung condition, which parameters are independent of air flow rates based on nitrogen monoxide content in exhalation, which content is dependent on air flow rates.

2. Description of the Prior Art

It is known that nitric oxide (NO) is produced in the lung and appears in the exhaled breath. The exhaled concentration is elevated in important inflammatory diseases such as asthma. A significant fraction of exhaled NO which is unique among endogenous gases comes from the airways. A single breath technique has been invented by one of the inventors and is the subject of a copending application in a prior application, which technique required inhalation to total lung capacity followed by a breath hold of up to 20 seconds followed by an exhalation with a decreasing flow rate which lasted approximately 15 seconds. Thus approximately 35 seconds was required to complete the maneuver. This duration is not possible for subjects who cannot follow directions (i.e., small children or subjects who are unconscious) or who have compromised lung function.

BRIEF SUMMARY OF THE INVENTION

The present invention is a technique to characterize nitric oxide exchange dynamics in the lungs during tidal breathing and thus represents a potentially robust technique that a wide range of subjects, including children, can perform. The technique is a breathing maneuver combined with a mathematical model, data filtering, and parameter estimation techniques to characterize the exchange dynamics of nitric oxide (NO) in the lungs.

In order to perform the technique, the subject breathes normally (tidally) into a mouthpiece while exhaled nitric oxide concentration and flow rate are recorded simultaneously. During the tidal breathing, the subject inspires NO-free air and the soft palate is either closed voluntarily or by applying a small negative pressure in the nasal cavity.

The exhaled NO concentration is separately simulated with a two-compartment model. The first compartment corresponds to the airways and the second compartment corresponds to the aveolar regions of the lungs. After data filtering and nonlinear least squares regression on the simulated exhaled NO concentration, the optimal values of three to six parameters were obtained. An objective of the simulation was to characterize NO exchange dynamics in both the airways and the alveolar regions.

Changes in lung volume for tidal breathing (400-800 ml) are smaller than for single breath maneuvers. A single cycle (inhalation and exhalation) occurs over a relatively short time frame (4-8 sec.), and exhalation profiles are observed in a narrow window (2-4 sec.). Over a single exhalation, there is little time to accumulate appreciable amounts of NO in the airway and alveolar components. Hence, tidal breathing profiles are flatter and lack the easily recognizable characteristics of the single breath maneuvers of the accepted techniques of the recent past. Furthermore, expired NO levels for tidal breathing are roughly 4-fold lower (5-10 ppb) than those observed for single breath maneuvers. Yet, the present technique provides a way of characterizing the NO exchange dynamics while the subject breathes tidally. That is, the subject breathes slowly and normally while at rest. Thus, advantageously, essentially any subject who can breathe into a mouthpiece can perform the test maneuver with no special training or skills (i.e., breath holding).

The invention can be used to quantify NO exchange dynamics and thus characterize metabolic and structural features not characterized by currently accepted techniques. The technique of the present invention is potentially most useful for longitudinally following subjects with inflammatory diseases. For example, a subject with asthma may breath tidally for two minutes while the NO concentration and flow rate are monitored. Our mathematical model and parameter estimation techniques would then estimate the flow-independent NO parameters. The subject may repeat this maneuver at regular intervals thereafter. Changes in the parameters in subsequent test maneuvers might prompt therapeutic intervention. This technique is also useful in achieving additional objectives with subjects having inflammatory diseases, such as monitoring the efficacy of the therapy during treatment.

In one aspect, the invention characterizes the same exchange dynamics while the subject breathes tidally, and in particular identifies the optimal breathing pattern. Thus, although other breathing patterns may be possible, they may require effort or time on the part of the subject.

As discussed above, nitric oxide (NO) is produced in the lung and appears in the exhaled breath. The exhaled concentration is elevated in important inflammatory diseases such as asthma. A significant fraction of exhaled NO arises from the airways, which NO is unique amongst endogenous gases. This aspect of the invention comprises a theoretical analysis to predict the optimum tidal breathing pattern to characterize nitric oxide exchange dynamics in the lungs.

Parametric characterization of nitric oxide (NO) gas exchange using a two-component model of the lungs as discussed above is a potentially promising, non-invasive technique to characterize inflammatory lung diseases. Until the advances of the present invention, this technique was limited to single breath maneuvers, including pre-expiratory breath hold, which is cumbersome for children and individuals with compromised lung function. The present invention applies the two-compartment model to parametric characterization of NO gas exchange from a tidal breathing pattern. This model's potential to estimate up to six flow-independent parameters. The model also aid in studying alternate breathing patterns, such as varying breathing frequency and inspiratory/expiratory flow rate ratio at constant alveolar ventilation rate. We identify four easily characterized flow-independent parameters, which include maximum airway flux, steady state alveolar concentration, airway volume, and deadspace volume (uncertainty <10%). Rapid inhalation followed by slow (long duration) exhalation as well as increasing the number of observed tidal breaths facilitates estimates of all flow independent parameters. The results demonstrate that a parametric analysis of tidal breathing data can be utilized to characterize NO pulmonary exchange.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 3 is a table summarizing the data shown in FIGS. 1A and 2A.

FIG. 7 is a table showing central, upper, and lower limits in accordance with the graph of FIG. 7 of the flow-independent parameter values $J'_{awNO}$, $D_{awNO}$, $\hat{D}_{alvNO}$, $C_{alv,ss}$, $V_{aw}$, and $V_{ds}$.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Single breath maneuvers can distinguish inflammatory diseases, such as asthma, cystic fibrosis, and allergic alveolitis, using either exhaled concentration alone, or more positional specific parametric characterization, such as airway diffusing capacity ($D_{awNO}$), maximum airway flux ($J'_{awNO}$) and steady state alveolar concentration ($C_{alv,ss}$). Single breath maneuvers may be difficult to perform, especially for children and individuals with compromised lung function. Hence the utility of tidal breathing to characterize NO exchange has been explored and is described herein.

Analysis of tidal breathing exhalation profiles presents new challenges relative to single breath maneuvers, such as smaller changes in lung volume and a shorter duration for exhalation. The shorter duration of exhalation reduces accumulation of NO in the airway compartment, resulting in expired NO levels, which are more than four-fold lower than those observed for single-breath maneuvers. Analyzing multiple consecutive tidal breaths potentially offsets this limitation.

The two-compartment model for tidal breathing includes both inhalation and exhalation intervals, as well as the time dependence of the alveolar concentration during exhalation. The initial alveolar concentration (at the start of the first full exhalation) is estimated by assuming all previous (unobserved) cycles (breaths) to be identical and consistent with the first cycle. Axial diffusion and detailed airway geometry are not included in the current version of the model. In addition, inhalation and exhalation flow rate profiles are approximated as constant over their respective intervals. The current version of the two-compartment model predicts a discontinuity in the expired NO profile at the end of airway evacuation, where the alveolar phase of exhalation begins. This discontinuity is most likely an artifact resulting from the assumptions of negligible axial diffusion, simplified airway geometry and ideal flow in the simulated system. If necessary, axial diffusion, more complex airway geometry, and less ideal flow can be incorporated into the model after its preliminary assessment using this simpler model.

Figure 1A:
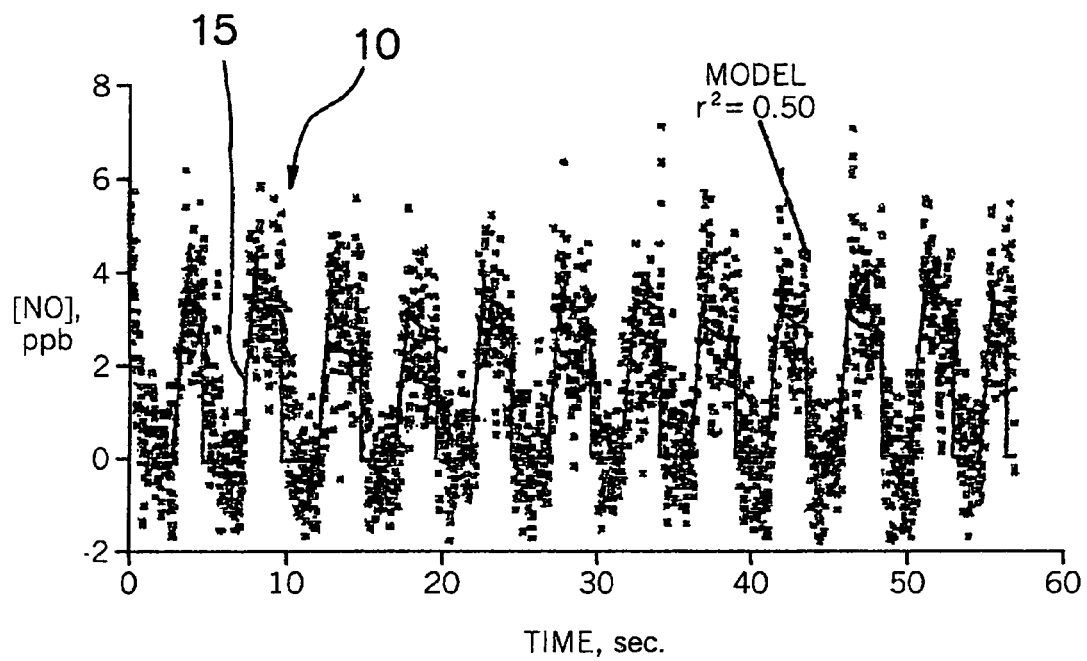
FIG. 1A is a graph showing a comparison between the model and the experimental data.
Figure 1B:
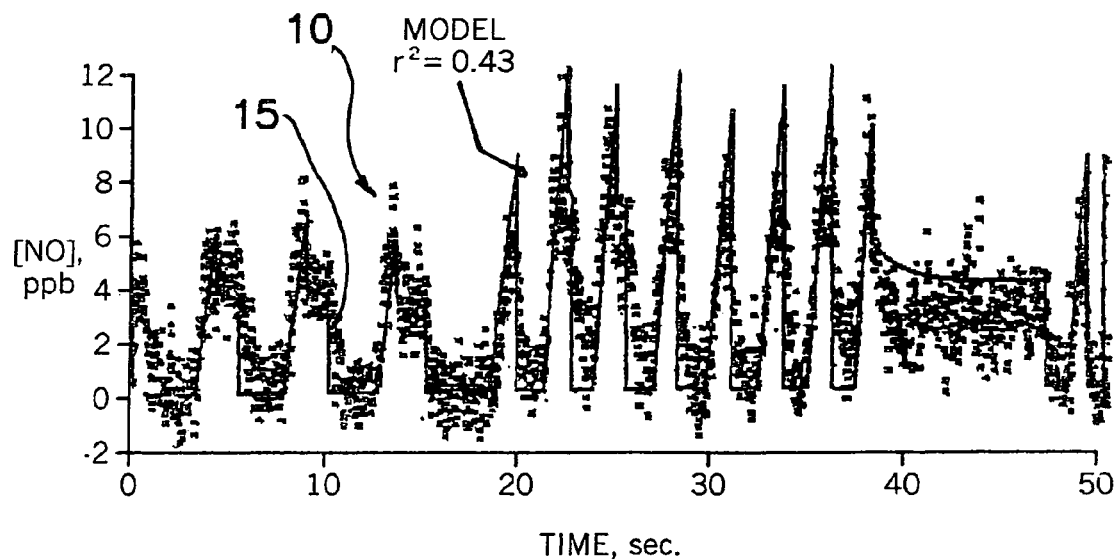
FIG. 1B is a graph similar to FIG. 1A having a different breath profile.

Two typical NO concentration profiles, each from 12 tidal breaths of an actual human subject, are illustrated in FIGS. 1A and 1B as identified by the peaks in NO against time. The subject was experienced at performing breathing maneuvers. Hence, minimal nasal contamination can be assumed. The observed data was sampled at 50 Hz and fitted to the model. FIGS. 1A and 1B compare the experimental data (indicated by x's 10) with the exhalation profiles predicted by the fitted two-compartment model (indicated by a solid line 15). The data set illustrated in FIG. 1A corresponds to normal tidal breathing (2,000-3,000 ml lung volume). In FIG. 1B, the first three breaths correspond to normal tidal breathing. However, breaths 4-10 of FIG. 1B correspond to higher lung volume (3,500-4,000 ml), with a prolonged expiration in the eleventh breath. Elevated levels of exhaled NO in breaths 4-11 are evident on inspection of FIG. 1B.

Figure 2A:
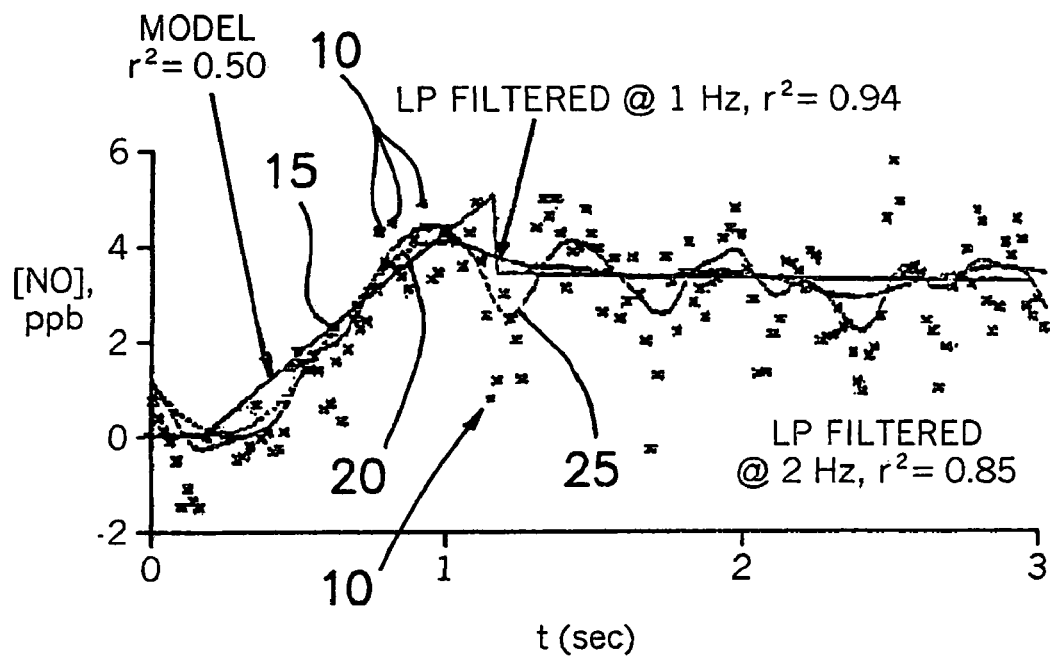
FIG. 2A is a detailed graph of the third breath of FIG. 1A and including filtered results.

FIG. 2A compares the experimental data (represented by x's 10) for the third breath of FIG. 1A with the exhalation profile predicted by the fitted two-compartment model (solid line 15). Expired NO concentrations are close to the lower detection limit. At these low levels, baseline fluctuations and noise, originating within analytical instrumentation, cause significant data scatter. Hence, uncertainties in observed NO concentrations significantly limit how close the parameter estimates come to the experimental data. Consequently, several different sets of parameter values are generally consistent with these data, although a high degree of uncertainty is associated with the parameter estimates.

Several techniques are available to minimize uncertainty in parameter estimates resulting from data scatter. The appropriate solution depends upon the source(s) of the error. During data acquisition, electronic noise (e.g., electromagnetic interference, smearing, aliasing, amplifier distortion, etc.) may be added to the signal. If the noise consists primarily of high frequency components, the signal may be filtered to resolve the underlying exhalation profile. This approach is called "low pass filtering", and the frequency at which the signal power is attenuated by 50% is referred to as the resolution bandwidth.

The dashed lines 20, 25 in FIG. 2A depict filtered data at resolution bandwidths of 1 and 2 Hz, respectively, and the filtered data show substantial improvement in their correlation with the fitted two-compartment model. This technique is useful for identification of data acquisition problems, and can increase the degree of confidence in parameter estimates, provided it is justified. However, since the true frequency spectrum of the signal is not known in advance, low pass filtering may inadvertently remove subtle features of the exhalation profile and is rigorously applicable only when the signal is contaminated by known systematic errors. In fact, spectral analysis of the NO analyzer baseline suggests that the dependence of noise amplitude upon frequency is subtle, with a broad spectrum typical for random ("white") noise rather than systematic errors.

In this case, a more efficacious approach is the Kalman Filter algorithm, which estimates the most probable exhalation profiles based on comparison of experimental observations with the model. It also forecasts probable values of physically meaningful system characteristics, called the state variables, which may not be directly observable. The state estimation feature of the Kalman Filter is potentially useful as a diagnostic tool to assess conditions within pulmonary tissue. Herein we consider only the basic Kalman Filter, which is applied for "on-line" removal of random error.

Figure 2B:
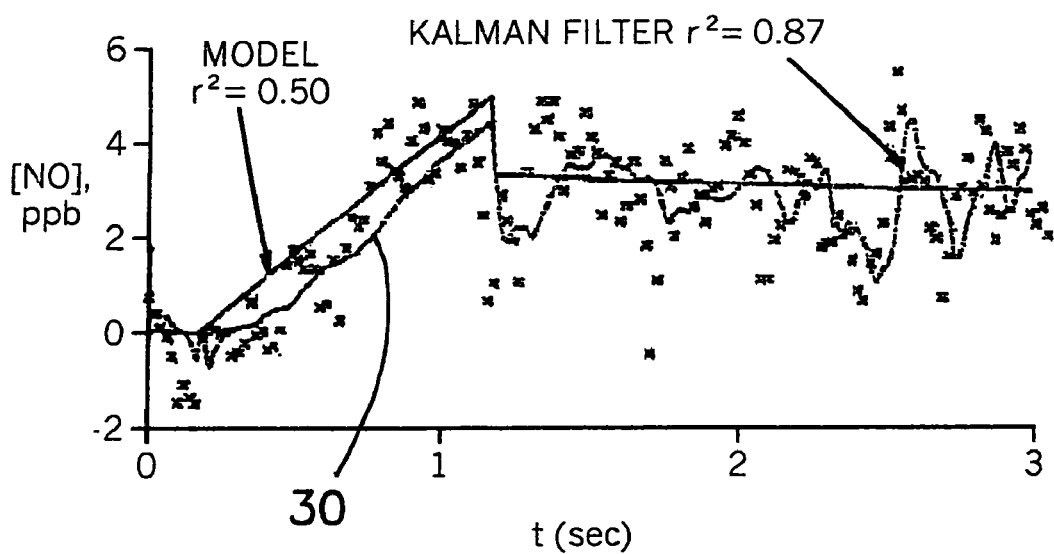
FIG. 2B is a detailed graph similar to FIG. 2A showing a special case of filtering.

Kalman filtered data (indicated as a dot-dash line 30 in FIG. 2B) is reasonably consistent with the fitted two-compartment model over the airway and alveolar evacuation phases of exhalation. However, during the airway evacuation phase, the exhalation profile predicted by the model lies above the filtered data, which implies systematic deviation from the model. Sinusoidal deviation from the model is evident during the alveolar evacuation phase. This may result from systematic errors (e.g., electronic noise, inadequacies in the model, etc), random errors ("white-noise"), or a combination of both.

We estimated six parameters ($D_{awNO}$, $J'_{awNO}$, $\hat{D}_{alvNO}$, $C_{alv,ss}$, $V_{aw}$ and $V_{ds}$) by minimizing a "score function", comprised of the sum of two appropriately scaled, mean-squared error terms. Both of these terms are fractions of the differences between observed and predicted NO concentrations for each of the 12 tidal breaths. The first term is the sum of the squared-differences between each sampled exhalation concentration and the model prediction. The second term compares the total amount of NO expired for each breath, as computed from the experimental data, with that predicted by the model. Selection of a score function should be made to reflect the most appropriate criterion for robust parameter estimation.

Predicted exhalation profiles are highly sensitive to the airway volume, $V_{aw}$, and the dead space volume, $V_{ds}$. Several parameter sets which fit the data, were found with $V_{aw}$ and $V_{ds}$ in the ranges: 180-220 and 20-50 ml, respectively. To simplify the statistical analysis presented herein, we fixed $V_{aw}$ and $V_{ds}$ at 200 ml and 40 ml, respectively. Hence, uncertainties were determined only for four parameters ($D_{awNO}$, $J'_{awNO}$, $\hat{D}_{alvNO}$, $C_{alv,ss}$).

Parameter estimates from the data depicted in FIGS. 1A and 2A are summarized in the table of FIG. 3, based on a minimum squared-error fit of the model with the data observed from 12 tidal breaths. We performed uncertainty analysis to compute 90% confidence intervals based on a joint parameter hypotheses. The unfiltered parameter estimates 35 depicted in the table of FIG. 3 show reasonable precision for $J'_{awNO}$ and $\hat{D}_{alvNO}$. The parameter estimates for both shown in Range column 40 were within ±20% at 90% confidence limits after 12 breaths. However, large uncertainties are associated with $D_{awNO}$ and $C_{alv,ss}$. By extrapolating the available data, we estimated the number of tidal breaths required to achieve parameter uncertainties within 5, 10, 25 and 50% of their mean values in column 45 (see the last four columns 50 of the table of FIG. 3). These estimates are based on joint parameter hypotheses at 90% confidence. Thus, $J'_{awNO}$ is easily characterized since its uncertainty is reduced to within 5% in only two breaths. However, to achieve the same precision, 120 breaths (more than 1,500 sampled exhalation concentrations) are required to characterize $\hat{D}_{alvNO}$, and 1,100 breaths are required for $C_{alv,ss}$. However, 12 breaths correspond to only about 2 minutes of sampling time. Thus, after 7 minutes (roughly 40 breaths) the uncertainty of $C_{alv,ss}$ is reduced to within 25%, and to within 10% after 45 minutes (260 breaths). Extrapolation of the unfiltered data suggests that $D_{awNO}$ can not be estimated for in the unfiltered scenario, irregardless of how many tidal breaths are monitored.

Reducing the parameter uncertainty was attempted by correlating the model with Kalman filtered data, which is shown by the parameter estimates 55. In principle the Kalman filter reduces "white noise", which in turn can reduce the "leverage effect" of outliers on parameter estimates. This method resulted in an increase in the correlation coefficient ($r^2$-value) from 0.50 to 0.87 (see dot-dash line in FIG. 2B) and significant reduction in the 90% confidence intervals for parameter estimates (see Kalman filtered results in the table of FIG. 3). This method also reduces the required number of tidal breaths to achieve the various parameter uncertainties ranges (see the last four columns 50 of the table of FIG. 3). For example, in contrast to the unfiltered results 35, only 8 breaths (less than 2 minutes) are required to determine $\hat{D}_{alvNO}/V_{alv}$ at a precision of ±10% in the filtered results 55. Although to achieve the same precision for $D_{awNO}$ and $C_{alv,ss}$ would require 5,400 breaths (about 15 hours) and 250 breaths (about 45 minutes), respectively, these results are encouraging since both random and systematic errors can be reduced further by applying more advanced versions of the Kalman Filter.

Figure 4:
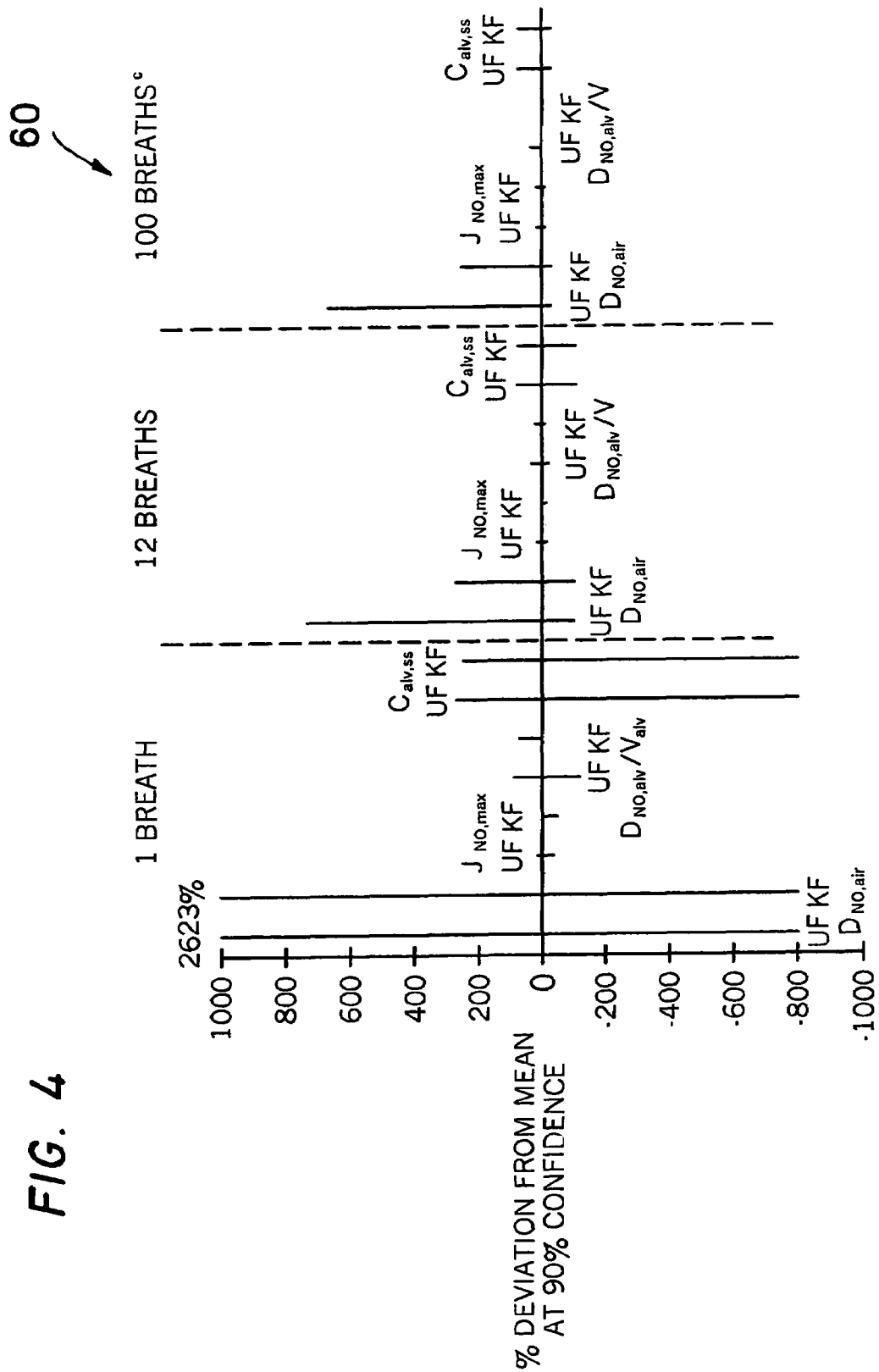
FIG. 4 is a graph showing the reduction in parameter uncertainty with the number of tidal breaths monitored.

The reduction in parameter uncertainty with the number of tidal breaths monitored is illustrated graphically in FIG. 4 which is a graph which shows for $D_{NO,air}$, $J_{NO,max}$, $D_{NO,air}/V_{alv}$ and $C_{alv,ss}$, the percent deviation from mean at 90% confidence for one breath, 12 breaths and 100 breaths, which is based on the joint parameter hypotheses at 90% confidence for both the unfiltered (UF) and the Kalman filtered (KF) correlations. Percentiles for 100 tidal breaths were extrapolated from the data for 12 tidal breaths and are shown at 60 in FIG. 4. After 100 breaths (roughly 20 minutes), the uncertainties of $J'_{awNO}$, $\hat{D}_{alvNO}/V_{alv}$, and $C_{alv,ss}$ are reduced to reasonable levels. However, $D_{awNO}$ remains poorly characterized. It is evident that $D_{awNO}$ and $C_{alv,ss}$ exhibit skewed distributions. Although this may be an artifact of the data extrapolation, it also suggests systematic deviation of the model in terms of its dependence on these parameters.

In the case of systematic deviation of the model from the observed exhalation profiles, more accurate parameter estimates can be achieved by upgrading the model to incorporate some of the additional features described above. On the other hand, if specific sources of electronic noise are identified, techniques, such as the low pass filtering scheme described above, can be applied. The Kalman Filter is the best way to minimize the adverse effect of random error. Finally, if all of the above sources of error are important, more advanced versions of the Kalman Filter are available to provide smoother estimates by combining the basic algorithm with other concepts, such as spectral analysis and the Principle of Maximum Likelihood. By using this "hybrid" approach, the most likely sources of error can be identified, and the most probable parameter estimates and their uncertainties can thereby be obtained.

Implementation of the Analysis

We have two primary goals. First, we explore the feasibility of estimating six flow-independent parameters, characteristic of NO gas exchange during tidal breathing, by fitting the two-compartment model to representative experimental tidal breathing data. In this assessment, we assume some knowledge of the extent of random noise introduced into experimental tidal breathing data, which result from the limitations of a typical analytical monitoring system. Our ultimate goal is to obtain estimates of the following flow-independent parameters from experimental tidal breathing data: airway diffusing capacity ($D_{awNO}$), maximum volumetric airway flux ($J'_{awNO}$), steady state alveolar concentration ($C_{alv,ss}$), alveolar diffusing capacity per unit alveolar volume ($\hat{D}_{alvNO}$), and the airway compartment and dead space volumes, $V_{aw}$ and $V_{ds}$, respectively.

Second, we explore a range of physiologically relevant tidal breathing patterns, and identify the pattern(s) that minimizes the uncertainty in parameter estimates per unit sampling time.

Model Structure and Assumptions

Figure 5:
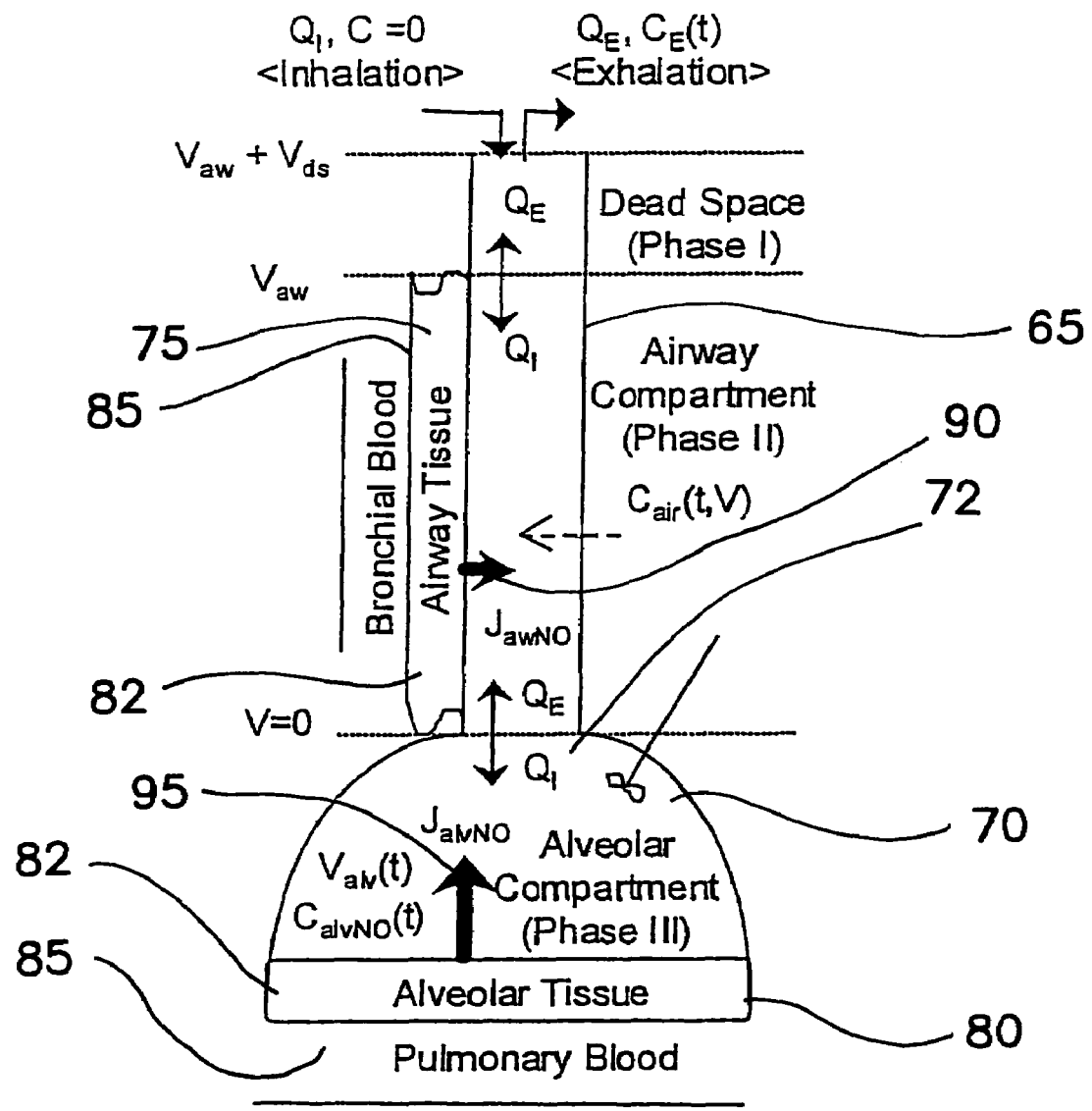
FIG. 5 is a schematic representation of the two-compartment model wherein exhaled nitric oxide has sources in both the alveolar ($J_{alvNO}$) and the airway ($J_{awNO}$) regions of the lungs, which represent the two compartments.

We utilize the previously described two-compartment model with minor modifications. Only the salient features of the model and its modifications are presented here. As shown in FIG. 5, we model the conducting airways (i.e., the trachea and the first 17 airway generations) and the respiratory bronchioles/alveolar region (generations 18 and beyond) as rigid and flexible compartments 65 and 70, respectively. These compartments together form the airspace 72. The bronchial mucosa 75 and alveolar membrane 80, respectively, provide airway tissue and alveolar tissue and surround the airway and alveolar compartments 65 and 70. Together, these tissues make up the exterior pulmonary tissue 82. NO is consumed by hemoglobin and other substrates present in pulmonary blood vessels, such that the NO concentration is zero at the exterior pulmonary tissue boundary 85 (located distal to the air space). Arrows 90 and 95 indicate net fluxes of endogenously produced NO, which diffuse into the air space 72 of the airway and alveolar compartments 65 and 70, are denoted $J_{awNO}$ and $J_{alvNO}$, respectively. On exhalation, NO is transported to the mouth by the convection of the bulk air stream, where it appears in expired breath.

Airway Region

A differential mass balance for the airway compartment 65 describes NO concentration in the airway gas space, $C_{air}=C_{air}(t,V)$, as a function of time, t, and axial position in units of cumulative volume, V, as derived in previous work. The airway compartment 65 is modeled as a cylinder with total volume $V_{aw}$, and axial diffusion is neglected. Thus, for both inhalation and exhalation:

$$\frac{\partial C_{air}}{\partial t} = -Q \frac{\partial C_{air}}{\partial V} + \hat{D}_{awNO}[C_{awNO} - C_{air}] \quad \text{(Equation 1)}$$

where Q is the volumetric flow rate of air ($Q=Q_I(t)$ for inhalation and $Q=Q_E(t)$ for exhalation). The net flux of NO into the airway is approximated as a linear function of $C_{air}$ as shown previously, $J_{awNO}=J'_{awNO}-D_{awNO}C_{air}=D_{awNO}[C_{awNO}-C_{air}]$, where $D_{awNO}$ is the airway diffusing capacity, $J'_{awNO}$ is the maximum volumetric airway flux, $C_{awNO}=J'_{awNO}/D_{awNO}$ is the equivalent gas phase airway tissue concentration, and $\hat{D}_{awNO}=D_{awNO}/V_{aw}$.

Figure 6A:
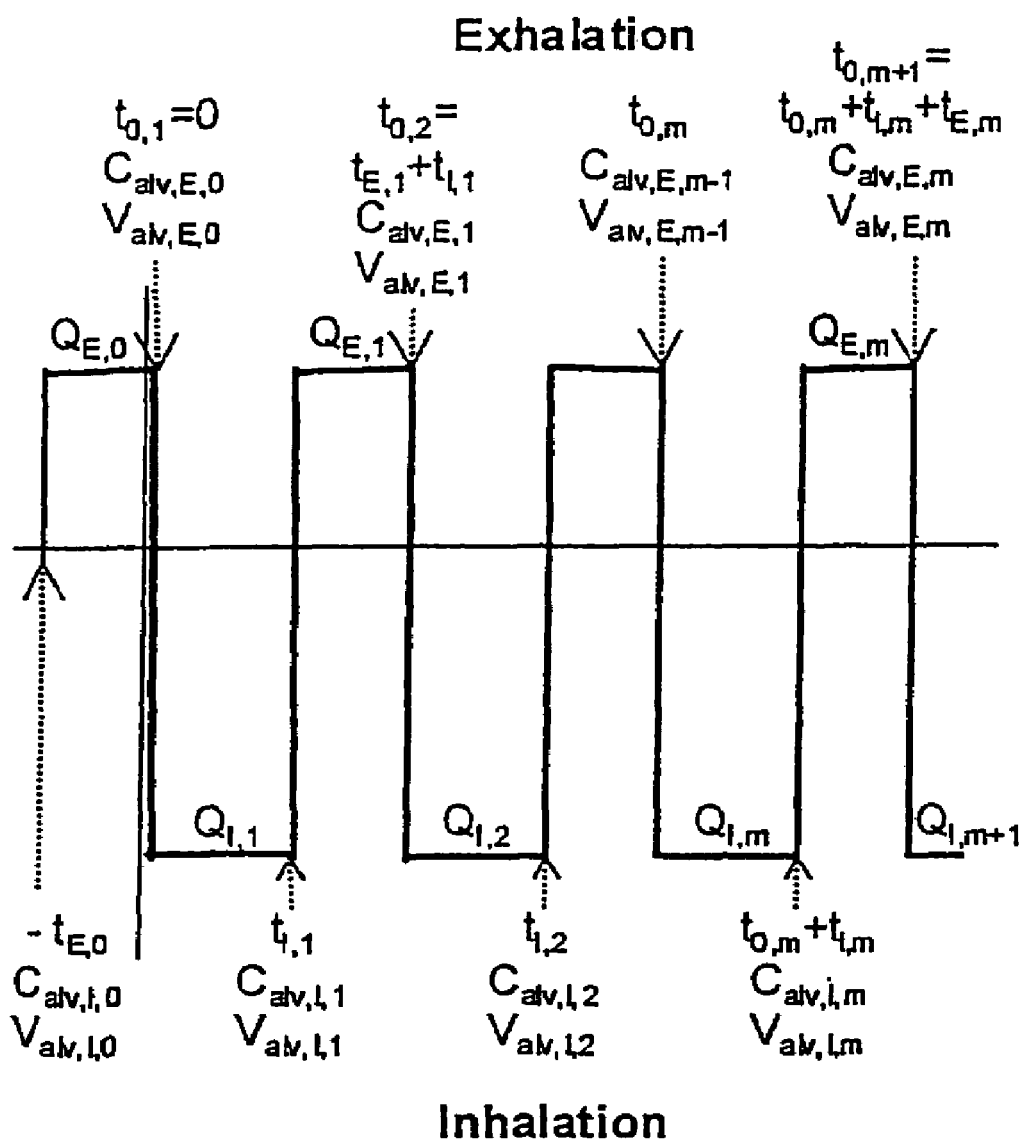
FIG. 6A is a graph depicting how the flow rate profile can be generally represented by a square wave in which the flow rates during inspiration and expiration are assumed constant.
Figure 6B:
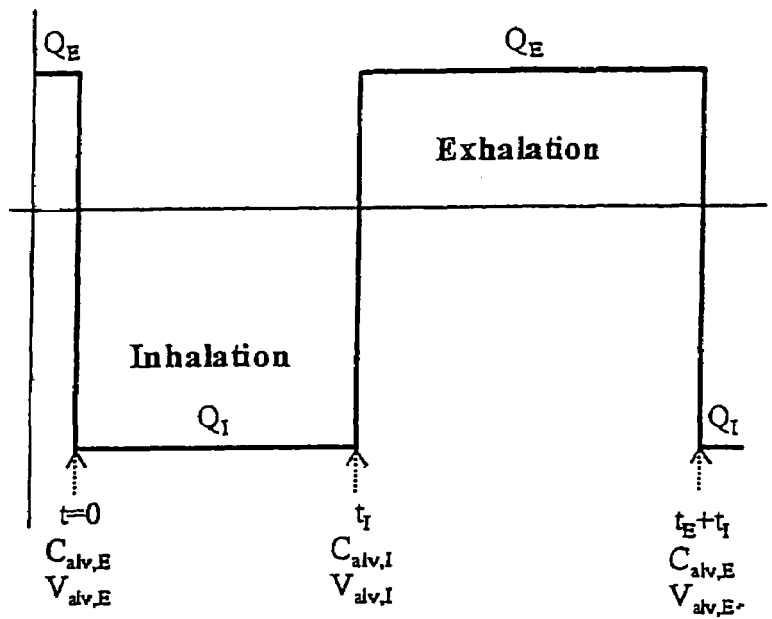
FIG. 6B is a schematic representation of a single tidal breath flow rate profile.

We assume that the initial condition for each exhalation is the final condition of the preceding inhalation, and the converse. From FIG. 5, appropriate boundary conditions are: $C_{air}(t,V=0)=C_{alv}(t)$, for exhalation, and $C_{air}(t,V=V_{aw}+V_{ds})=0$, for inhalation (NO free air source). For arbitrary flow rate profiles, a rigorous solution to Equation 1 above is obtained in terms of airway residence time functions, as described previously. Herein, we approximate the inhalation and exhalation flow rate profiles, $Q_I(t)$ and $Q_E(t)$, as square-wave functions, represented by their respective time-weighted-averages, $\bar{Q}_I$ and $\bar{Q}_E$, over each time interval as depicted in the graphs of FIGS. 6A and 6B. Thus, $C_{air}(t,V)$, can be expressed as an array of algebraic expressions within the airway ($0<V<V_{aw}$) and the dead space regions ($V_{aw}<V<V_{aw}+V_{ds}$), over the inhalation and exhalation time intervals (see the Model Solution for Square-wave Flow Rate Profiles section below). The exhalation profile, $C_E(t)$, is determined by evaluating $C_{air}(t,V=V_{aw}+V_{ds})$ on the exhalation time interval.

Alveolar Region

A differential mass balance for NO in a well-mixed alveolar compartment, valid for both inhalation and exhalation was derived. The time dependence volume of NO concentration in the alveolar gas space, $C_{alv}(t)$, is governed by:

$$dC_{alv}/dt=\hat{D}_{alvNO}[C_{alv,ss}-C_{alv}]-Q(C_{air,end}-C_{alv})/V_{alv}(t) \quad \text{(Equation 2)}$$

where $C_{air,end}=C_{air}(t,V=0)$ for inhalation, and $C_{air,end}=C_{alv}(t)$ for exhalation. The alveolar volume, $V_{alv}(t)$, is related to the flow rate by: $dV_{alv}/dt=-Q_I$ where $Q=Q_I$ for inhalation and $Q=Q_E$ for exhalation (see FIG. 5). We approximate the net flux of NO into the alveolar tissue gas space as: $J_{alvNO}=J'_{alvNO}-D_{alvNO}C_{alv}(t)=D_{alvNO}[C_{alv,ss}-C_{alv}(t)]$, where $J'_{alvNO}$ is the maximum volumetric flux of NO into the alveolar compartment and $C_{alv,ss}$ is the steady state, mixed alveolar concentration. $D_{alvNO}$ is the diffusing capacity of NO in the alveolar region, which we express per unit alveolar volume as: $\hat{D}_{alvNO}=D_{alvNO}/V_{alv}$.

Previous work has demonstrated that $C_{alv}(t)$ approaches $C_{alv,ss}$ for breath-hold times exceeding 10 s. However, for tidal breathing, we must determine the time dependence of $C_{alv}(t)$. Other studies have shown that $D_{alvNO}$ is roughly proportional to $(V_{alv})^{2/3}$. Thus, alveolar diffusing capacity per unit alveolar volume, $\hat{D}_{alvNO}$, is proportional to $(V_{alv})^{-1/3}$. A rough sensitivity assessment implies that the percent variation in $\hat{D}_{alvNO}$ is roughly one-third of the relative change in tidal volume, $\Delta V_{alv}/V_{alv}$. Thus, for a typical tidal breath, where $\Delta V_{alv}/V_{alv}$ is 15%, we expect only 5% variation in $\hat{D}_{alvNO}$, which is comparable to current experimental estimates. Herein, we assume $\hat{D}_{alvNO}$ is a constant (flow-independent) parameter. Systematic errors, resulting from this assumption increase in significance as $\Delta V_{alv}/V_{alv}$ increases.

Model Solution for Identical Breaths

All of our analysis assumes that each breath is identical and a dynamic steady state is maintained in vivo. This results in a periodic exhalation profile. However, this is usually not observed in practice. A more general solution, which allows the flow rates and time intervals of inhalation and exhalation to vary with each breath, can be derived to model actual tidal breathing data (see the Model Solution for Square-wave Flow Rate Profiles section below). For identical breaths, we model only the first observed breath, and denote the flow rates and time intervals as simply $Q_I$, $Q_E$, $t_I$ and $t_E$, for inhalation and exhalation, respectively (see FIGS. 6A and 6B). Square-wave flow rate profiles are shown in FIG. 6A. FIG. 6B shows one period of the square-wave profile of FIG. 6A. The residence times for the airway (a) and dead space (ds) compartments are: $\tau_{Ea} = V_{aw}/Q_E$ and $\tau_{Eds} = V_{ds}/Q_E$ (exhalation), and $\tau_{Ia} = V_{aw}/Q_I$ and $\tau_{Ids} = V_{ds}/Q_I$ (inhalation). We assume that the tidal volume change, $\Delta V_{alv}$, exceeds the sum of the airway and dead space volumes, $V_{aw} + V_{ds}$ (i.e., $t_E > \tau_{Ea} + \tau_{Eds}$ and $t_I > \tau_{Ia} + \tau_{Ids}$). Integration of Equation 1 yields an analytical solution, for the NO concentration profiles, $C_{air}(t,V)$, which allows us to express the exhalation profile, $C_E(t) = C_{air}(t, V = V_{aw} + V_{ds})$, in terms of the initial alveolar concentration, $C_{alv}(t=t_0+t_I) = C_{alv,I}$.

The exhalation profile is divided into the classic three phases representing the deadspace (Phase I), and airway compartment (Phase II), and the alveolar compartment (Phase III). The profile shown is only representative of the NO exhalation profile during tidal breathing; the precise shape of the exhalation profile for NO depends on the values of the flow-independent parameters as shown in FIGS. 9A-9F and discussed below.

For identical breaths, $C_E(t)$ reduces to:

$$\overline{S}_j^{sr,rms}$$

Phase I: $t_I \leq t < t_I + \tau_{Eds}$:

$$C_E(t) \times 0 \quad \text{(Equation 3)}$$

Phase II: $t_I + \tau_{Eds} \leq t < t_I + \tau_{Eds} + \tau_{Ea}$:

$$C_E(t) = C_{awNO}[1 - e^{(-D_{awNO}(1+q^{-1})(t-t_I-\tau_{Eds}))}] \quad \text{(Equation 4)}$$

Figure 6C:
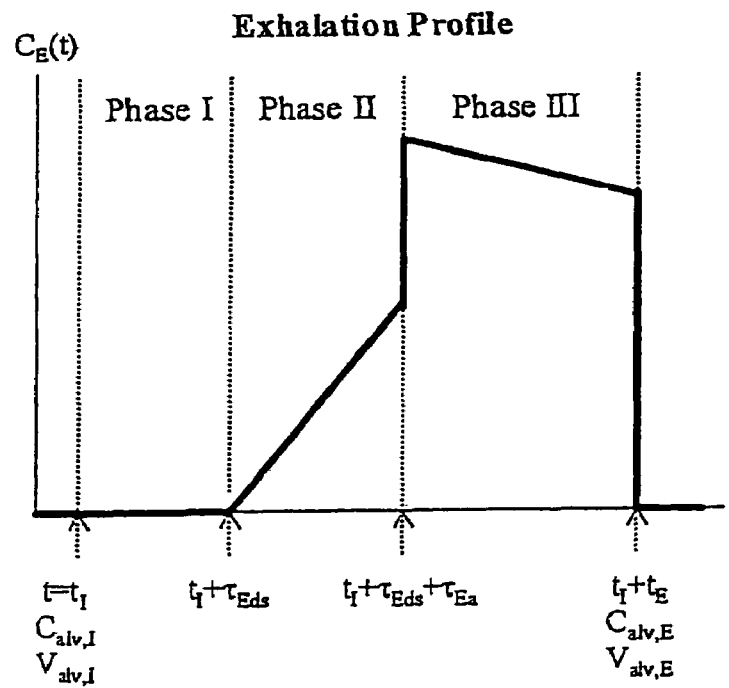
FIG. 6C is a schematic representation of a single tidal breath exhalation profile.

Phase III: $t_I + \tau_{Eds} + \tau_{Ea} \leq t < t_I + t_E$:

$$\begin{aligned} C_E(t) &= C_{awNO} + [C_{alv,ss} - C_{awNO}] \\ &\quad [e^{(-D_{awNO}\tau_{Eds})}] + (C_{alv,I} - \\ &\quad C_{alv,ss})e^{(D_{awNO}\tau_{Eds} - \hat{D}_{alvNO}(t-t_I-\tau_{Eds}-\tau_{Ea}))} \end{aligned} \quad \text{Equation 5}$$

where $q = Q_I/Q_E = t_E/t_I$. The shape of a typical exhalation profile is depicted graphically in FIG. 6C. Phase I (Equation 3) corresponds to the exhalation of NO free air from the dead space region. Phase II (Equation 4) corresponds to the exhalation of air, originating from the airway compartment at the start of exhalation. Phase III (Equation 5) describes the exhalation of air, originating from the alveolar compartment, which passes through the airway and dead space compartments on its way to the mouth (see FIG. 6C).

For the alveolar region, we denote the final conditions of each inhalation and exhalation with the subscripts, E and I, respectively. Thus, for the first observed inhalation (t=0 to $t_I$), Equation 2 is subject to the initial conditions: $C_{alv}(t=0) = C_{alv,E}$ and $V_{alv}(t=0) = V_{alv,E}$. Similarly, for exhalation (t=$t_I$ to $t_I+t_E$), Equation 2 is subject to the initial conditions: $C_{alv}(t=t_I) = C_{alv,I}$ and $V_{alv}(t=t_I) = V_{alv,I}$. For square-wave flow rate profiles the alveolar volume is given by $V_{alv}(t) = V_{alv,E} + Q_I t$ for inhalation and $V_{alv}(t) = V_{alv,I} - Q_E(t-t_I)$ for exhalation. An algebraic expression for $C_{alv,I}$ is derived by direct integration of Equation 2 over the previous inhalation and exhalation time intervals:

$$\begin{aligned} C_{alv,I} &= Q_I [f_t C_{awNO} - f_a C_{alv,ss}]/[V_{alv,I} - \\ &\quad V_{alv,E} e^{(\hat{D}_{alvNO}(t-t_I-\tau_{Eds}-\tau_{Ea}))}] - Q'_I f_{QI}] + C_{alv,ss} \end{aligned} \quad \text{(Equation 6)}$$

where $f_t$, $f_a$ and $f_{QI}$ are functions of $D_{awNO}$, $\hat{D}_{alvNO}$, $V_{aw}$, $V_{ds}$, $Q_I$, $Q_E$, $t_I$ and $t_E$, as defined in the Nomenclature and Abbreviations section below. The above assumptions imply that the initial alveolar concentration, $C_{alv,I,1}$, for the first observed exhalation is the same as that for the previous (unobserved) exhalation, $C_{alv,I,0}$ (see the Model Solution for Square-wave Flow Rate Profiles section below).

Model Solution for Square-Wave Flow Rate Profiles

An analytical solution can be derived for Equations 1 and 2 for square-wave flow rate profiles and a general breathing pattern. We index each breath by the subscript, m, which starts at m=1 for the first observed breath (m=0 for the previous, unobserved breath). Each inhalation begins at time $t_{0,m}$ = Summation from i=1 to m-1 of $[t_{I,i}+t_{E,i}]$, where $t_{0,1}=0$ at the start of the first observed inhalation. Thus, $Q_{I,m}$ and $Q_{E,m}$ represent the inhalation and exhalation flow rates averaged over their respective time intervals, $t_{I,m}$ and $t_{E,m}$ (e.g., $Q_{I,1}$ and $Q_{E,1}$ on the time intervals, t=0 to $t_{I,1}$, and $t_{I,1}$ to ($t_{I,1}+t_{E,1}$), respectively, for the first observed breath).

For breath, m, we define the residence times of the airway (a) and dead space (ds) compartments, for inhalation (I) and exhalation (E), as $\tau_{Ia,m} = V_{aw}/Q_{I,m}$, $\tau_{Ids,m} = V_{ds}/Q_{I,m}$, $\tau_{Ea,m} = V_{aw}/Q_{E,m}$, and $\tau_{Eds,m} = V_{ds}/Q_{E,m}$, respectively. Integration of Equation 1 yields an analytical solution for the NO concentration profiles, $C(t,V)$, within the airway (V=0 to $V_{aw}$) and the dead space regions (V=$V_{aw}$ to $V_{aw}+V_{ds}$), from which we obtain the exhalation profile, $C_E(t) = C_{air}(t, V = V_{aw}+V_{ds})$ on the exhalation time interval, t=$t_{0,m}+t_{I,m}$ to $t_{0,m+1}$. This solution is analogous to those for Equations 3 to 5, which are omitted for brevity.

The initial, alveolar region conditions, for inhalation and exhalation, are equated to the final conditions of each exhalation and inhalation (denoted by the subscripts E and I), respectively. Thus, $C_{alv}(t)$ and $V_{alv}(t)$ are evaluated as: $C_{alv,E,m-1}$, $V_{alv,E,m-1}$, $C_{alv,I,m}$ and $V_{alv,I,m}$ at: t=$t_{0,m}$ and $t_{0,m}+t_{I,m}$, respectively. For the general case, we assume the ratio, $q_1 = Q_{I,1}/Q_{E,1} = t_{E,1}/t_{I,1}$, for the first observed breath is identical to all previous (unobserved) breaths, which implies that the initial alveolar concentration, $C_{alv,I,1}$, for the first observed exhalation is identical to that for the previous (unobserved) exhalation, $C_{alv,I,0}$. Finally, we relate the initial conditions for consecutive exhalations, $C_{alv,m}$ and $C_{alv,I,m-1}$:

$$\begin{aligned} C_{alv,I,m} &= (C_{alv,I,m-1} - C_{alv,ss})[V_{alv,E,m-1} e^{(-\hat{D}_{alvNO}(t_{I,m}+t_{E,m-1}))} + Q_{I,m} f_{QI,m}]/V_{alv,I,m} + Q_{I,m}[f_{t,m} \\ &\quad C_{awNO} - f_{a,m} C_{alv,ss}]/V_{alv,I,m} + C_{alv,ss} \end{aligned} \quad \text{(Equation 7)}$$

where $f_{t,m}$, $f_{a,m}$ and $f_{QI,m}$ are defined in analogous fashion to $f_t$, $f_a$ and $f_{QI}$, respectively (see the Nomenclature and Abbreviations section at the end of the detailed description). For the special case of "dynamic steady state" (i.e., identical breaths) the exhalation profile is periodic, with period, $t_I+t_E$, and we may drop the subscript, m, for: $Q_{I,m}$, $Q_{E,m}$, $t_{E,m}$, $t_{I,m}$, $V_{alv,E,m}$, $V_{alv,I,m}$, $C_{alv,E,m}$, $C_{alv,I,m}$, $f_{t,m}$, $f_{a,m}$, and $f_{QI,m}$. Thus, for identical breaths, Equation 7 reduces to Equation 6.

Confidence Intervals

We computed theoretical confidence intervals (uncertainties) for hypothetical estimates of the six flow-independent parameters (defined above) from experimental tidal breathing data using the two-compartment model: $D_{awNO}$, $J'_{awNO}$, $C_{alv,ss}$, $\hat{D}_{alvNO}$, $V_{aw}$, and $V_{ds}$. In practice, $\hat{D}_{alvNO}$, $V_{aw}$ and $V_{ds}$, are usually specified, based on previous experiments, morphology, and sampling system characteristics. However, we assess the efficacy of estimating these additional parameters from exhalation profile data, herein.

The Sensitivity an Uncertainty Analysis section below describes the methodology used to compute theoretical 90% confidence intervals for the estimated flow-independent parameters, $X_j$. We express our results in terms of the fractional uncertainties, $\Delta x_j$ (indexed by j=1, 2, . . . , P=6), or the fractional deviation from the "unbiased" or central value:

$$\Delta x_j = (X_j - X_{j,0})/X_{j,0} \qquad \text{(Equation 8)}$$

Experimental measurement error is expressed as the concentration difference, $Y(t) = [C_E(t) - C_D(t)]$, where $C_E(t)$ and $C_D(t)$ represent the NO exhalation profiles predicted by the model and observed in hypothetical measurements, respectively. We assume that $Y(t)$ is a Gaussian white noise sequence with zero mean and variance, $\sigma_{ED}^2$, which results from random baseline fluctuations with a nominal standard deviation of $\sigma_{ED} = \pm 1$ ppb. The observed data is assumed to be sampled at 50 Hz, corresponding to a sampling time, $T_s = 0.02$ s. Thus, for each exhalation, m, we can define the discrete time difference, $t - t_{0,m} - t_{I,m} = nT_s$ (n=0, 1, 2, . . . , $N_m$), where the total number of sampled concentrations for tidal breath, m, is: $N_m = t_{E,m}/T_s$. Hence, for each breath, we represent $Y(t)$ as a discrete sequence, $Y(n)$, comprised of $N_m$ independent and normally distributed random variables. Thus, in general, a sequence of M breaths includes L=Summation from m=1 to M of $N_m$ independent and normally distributed samples, each with variance $\sigma_{ED}^2$, and zero mean.

Sensitivity, an Uncertainty Analysis

We characterize the accuracy of a particular, flow-independent parameter estimate as the 90% confidence interval of parameter, $X_j$, around its fitted value, $X_{j,0}$, with the other parameters, $X_i$ (i≠j), fixed at their fitted values, $X_{i,0}$. Statistically, we define the 90% confidence interval, $X_{j,U} \geq X_j \geq X_{j,L}$, as the range of variation in $X_j$ around $X_{j,0}$, over which there is 90% probability that $X_j$ does not influence the error, $Y(n)$. Thus, $X_{j,U}$ and $X_{j,L}$ are the upper and lower limits of $X_j$ at 90% probability.

If a single parameter, $X_j$, is varied around $X_{j,0}$, with the other parameters fixed at their fitted values, $X_i = X_{i,0}$ (i≠j), then $C_E(n) = C_E(n, X_j, X_{i,0})$ is a function of the flow-independent parameters, which for the best unbiased estimate, $X_j = X_{j,0}$, is: $C_{E,0}(n) = C_E(n, X_{j,0}, X_{i,0})$. However, the sequence, $Y_0(n) = [C_{E,0}(n, X_{j,0}, X_{i,0}) - C_D(n)]$, is a random variable, whereas $Y(n) - Y_0(n) = [C_E(n, X_j, X_{i,0}) - C_{E,0}(n, X_{j,0}, X_{i,0})]$ is a predetermined function of the model parameters and time, $t = nT_s + t_{0,m} + t_{I,m}$. With these assumptions, we may estimate parameter confidence intervals, based on a simple t-test, for known variance, $\sigma_{ED}^2$:

$$\sum_{n=1}^{L} [C_E(n, X_i, X_{i,0}) - C_{E,0}(n, X_{j,0}, X_{i,0})]^2 = \sigma_{ED}^2 T(L-P)^2 \qquad \text{(Equation 9)}$$

where $T(L-P)$ is the critical t-value at 90% confidence with L-P degrees of freedom, and where $X_{j,0}$ is the hypothetical fitted value of flow-independent parameter and $X_j$ is its value at a 90% confidence limit (i.e., either $X_{j,U}$ or $X_{j,L}$).

If $C_E(n, X_j, X_{i,0})$ is a linear function of $X_j$, for $X_{j,U} \geq X_j \geq X_{j,L}$, then the relationship, $\Delta X_j = X_{j,U} - X_{j,0} = X_{j,0} - X_{j,L}$, holds and the 90% confidence limit of $X_j$ is expressed in terms of its fractional uncertainty, $\Delta x_j = \Delta X_j/X_{j,0}$. This is valid whenever $C_E(n, X_j, X_{i,0})$ is approximately linear in $X_j$ around $X_{j,0}$. In this case: $Y(n) - Y_0(n) = S_j(n) \Delta X_j$, where $S_j(n)$ is the sensitivity of $C_E(n, X_j, X_{i,0})$ with respect to $X_j$. We also define the normalized or relative sensitivity, $S^r_j$, and the semi-relative sensitivity, $S^{sr}_j$, which represent the fractional and absolute change of $C_E$ per fractional change in $X_j$, respectively. These three quantities are related to each other as shown below:

$$S_j(n) = \frac{\partial C_E(n, X_j, X_{i,0})}{\partial X_j} \text{ where } X_j = X_{j,0} \qquad \text{(Equation 10)}$$
$$= C_E(n, X_{j,0}, X_{i,0}) S^r_j(n) / X_{j,0} = S^{sr}_j(n) / X_{j,0}$$

Thus, if $C_E(n, X_j, X_{i,0})$ is a linear function of $X_j$, Equation 9 reduces to:

$$\Delta X_j \bar{S}[S_j(n)]^2\}^{1/2} = \Delta x_j \sum_{n=1}^{L} [S^{sr}_j(n)]^2\}^{1/2} \qquad \text{(Equation 11)}$$
$$= \pm \sigma_{ED} T(L-P)$$

Since $S^{sr}_j(t)$ is a function of time, we define the time-averaged, root-mean-squared semi-relative sensitivity, $|\bar{S}^{sr,rms}_j|$, by averaging over each exhalation time interval, ($t = t_{0,m} + t_{I,m}$ to $t_{0,m} + t_{I,m} + t_{E,m}$):

$$|\bar{S}^{sr,rms}_j|^2 = (1/(L-P)) \sum_{n=1}^{L} [S^{sr}_j(n)]^2 \qquad \text{(Equation 12)}$$

The quantity, (L–P), appears in Equation 12 as a correction for degrees of freedom. Thus, if $|\bar{S}^{sr,rms}_j|$ is sufficiently large, $\Delta X_j$ is small and $X_j$ can be accurately determined, or if $|\bar{S}^{sr,rms}_j|$ is small, $\Delta X_j$ is large. Thus, we express the 90% confidence intervals for individual, parameter hypotheses in terms of theoretical fractional uncertainties by combining Equations 11 and 12 to obtain:

$$\Delta X_j = \pm \sigma_E T(L-P)/\{[L-P]^{1/2} |\bar{S}^{sr,rms}_j|\} \qquad \text{(Equation 13)}$$

Equation 13 is valid if $C_E(n, X_j, X_{i,0})$ can be expressed as a linear function of $X_j$ on the interval, $X_{j,U} \geq X_j \geq X_{j,L}$. Our results suggest that this is true for $X_j = D_{awNO}$, $J'_{awNO}$ and $C_{alv,ss}$. However, $\hat{D}_{alvNO}$, $V_{aw}$ and $V_{ds}$ exhibit non-linear behavior and their confidence intervals are computed from Equation 9, for these flow-independent parameters. For the latter case, unless otherwise indicated, $\Delta x_j = \Delta X_j/X_{j,0}$ is evaluated for $\Delta X_j$ set equal to the maximum of $X_{j,U} - X_{j,0}$ or $X_{j,0} - X_{j,L}$.

The assumption of independent and identically distributed random variables is not valid if there is systematic deviation between the observed data and predictions of the model. Nonetheless, the methodology presented above yields preliminary estimates for parameter uncertainties, which can be used to design experimental protocols.

We computed the uncertainties of parameter estimates by using the t-statistic-set forth above. As discussed above, theoretical exhalation profiles are linear functions of $J'_{awNO}$ and $C_{alv,ss}$, and may be approximated as a linear function of $D_{awNO}$. Thus, we computed their fractional uncertainties from Equations 12 and 13 above. However, $D_{alvNO}$, $V_{aw}$ and $V_{ds}$ exhibit non-linear behavior; thus, we computed $\Delta x_j$ from Equation 9 above for these parameters. We analyzed the impact of the parameter value, the number of observed tidal breaths, and the breathing pattern on the confidence intervals.

Effect of Flow-Independent Parameter Values

Flow-independent parameters demonstrate significant inter-subject variability, and thus the confidence interval for a given parameter may vary. We studied the impact of the parameter value itself on the uncertainty by individually varying each parameter with the other parameters fixed at their central values. Thus, we performed our simulations with pre-selected central, lower and upper limit values for the flow-independent parameters (see the table of FIG. 7). The set of parameter values used for each simulation correspond to the hypothetical best, unbiased estimates, $X_{j,0}$, determined experimentally.

Effect of the Number of Observed Tidal Breaths

A potential advantage of tidal breathing relative to the single breath maneuver is the ability to easily observe multiple consecutive breaths which may reduce the uncertainty in the estimated parameter value. Equations 9, 12 and 13 predict that $\Delta x_j$ decreases as the total number of samples, L, increases. Specifically, $\Delta x_j \to 0$, as $L \to \infty$. Thus, parameter uncertainties, which are exclusively the result of white noise (random errors), vanish for a large number of samples. Herein, we do not account for potential systematic errors (e.g., The variation of $\hat{D}_{alvNO}$, resulting from its dependence upon alveolar volume, or $\Delta V_{alv}$, as discussed above). Unlike parameter uncertainties resulting from random errors, uncertainties resulting from systematic errors will not necessarily vanish for a large number of samples.

Effect of Breathing Pattern

Sustainable tidal breathing requires a minimum alveolar ventilation rate, $\dot{V}_{alv}$, to supply oxygen to metabolizing tissue, which we specify as: $\dot{V}_{alv} = [\Delta V_{alv} - V_{aw} - V_{ds}]/(t_I + t_E) = 5{,}000$ ml/min, where $\Delta V_{alv} = Q_I t_I = [V_{alv,I} - V_{alv,E}]$ is the tidal volume change (i.e., equivalent to the change in alveolar volume). For identical breaths (governed by Equations 3 to 6), the breathing pattern is completely characterized by the flow rate ratio, $q = Q_I/Q_E = t_E/t_I$, and the breathing frequency, $f_B = q/[(1+q)t_E]$. Thus, $f_B$ and q were varied at fixed $\dot{V}_{alv}$ to specify the breathing pattern. We specify central values $q=2$ and $f_B=0.2$ s$^{-1}$=12 min$^{-1}$, which correspond to: $\Delta V_{alv}=992$ ml, $Q_E=207.5$ ml/s, $Q_I=415$ ml/s, $t_E=3.33$ s, and $t_I=1.67$ s. By varying q and $f_B$ around their central values, we can identify breathing patterns, which minimize the uncertainties of flow-independent parameter estimates.

As a basis for this analysis, we impose the upper limit: $V_{alv,I} \leq 5{,}000$ ml, and specify the initial alveolar volume, $V_{alv,E}=2{,}300$ ml, which corresponds to a maximum tidal volume change of $\Delta V_{alv,max}=[V_{alv,I}-V_{alv,E}]_{max}=2{,}700$ ml. For identical breaths this specifies a lower limit for the breathing frequency, $f_B \leq \dot{V}_{alv}(\Delta V_{alv,max}-V_{aw}-V_{ds})$, which at the central values, $V_{aw}=200$ ml and $V_{ds}=75$ ml, becomes: $f_B \geq (5{,}000$ ml/min)/(2,425 ml)$\approx 2$ breaths/min. $\Delta V_{alv}$ is constrained further by requiring: $\tau_{Ia} + \tau_{Ids} \leq t_I$ and $\tau_{Ea} + \tau_{Eds} \leq t_E$.

Results

Effect of Flow-Independent Parameter Values

We computed 90% confidence intervals for each flow-independent parameter after one minute of tidal breathing by individually varying each parameter, while fixing the other parameters at their central values (see the table of FIG. 7). We kept the control variables, q and $f_B$, at 2 and 12 min$^{-1}$, respectively, in this analysis. These results are shown in FIGS. 8 and 9.

Figure 8:
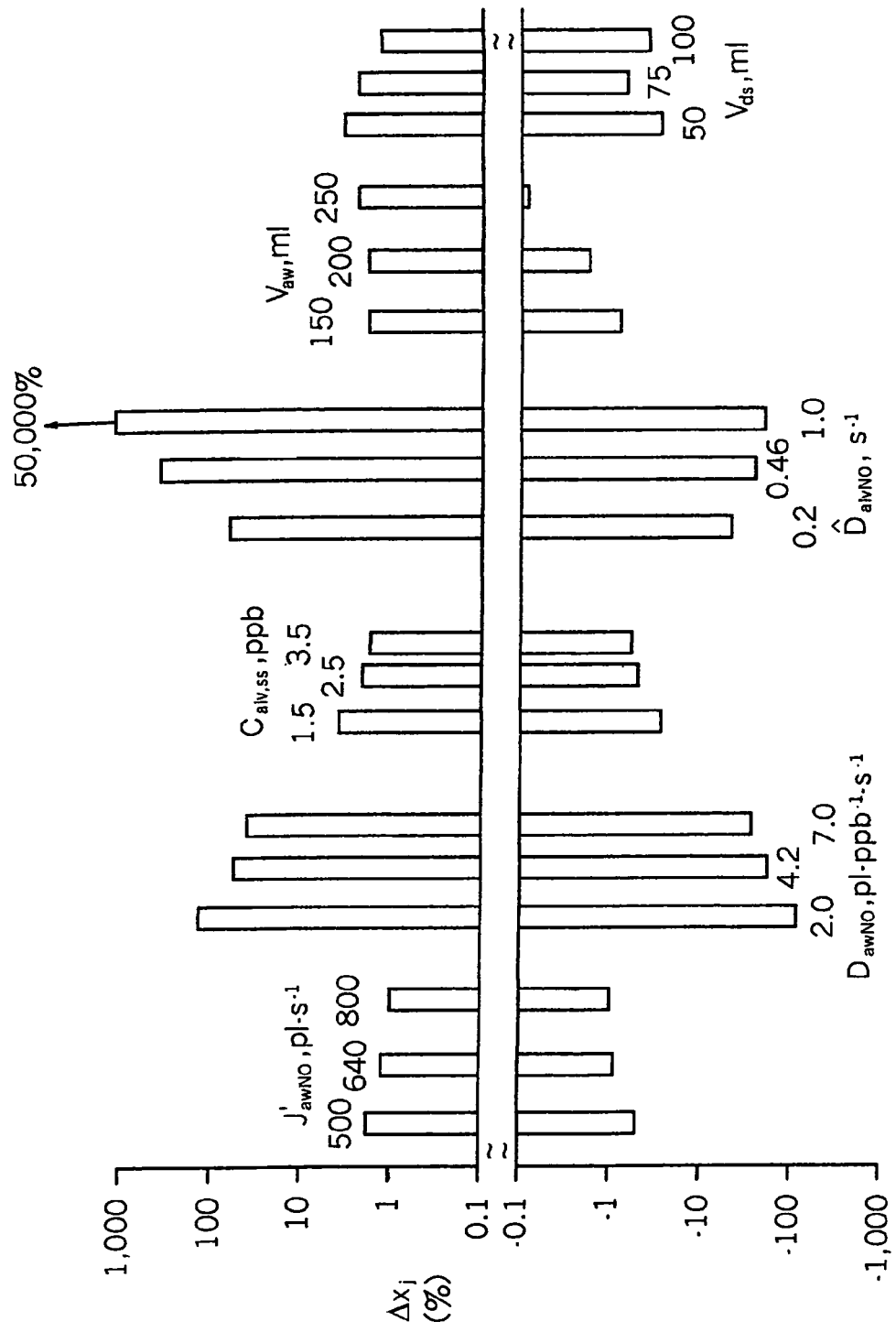
FIG. 8 is a graph showing fractional uncertainties, $\Delta x_j$, of the flow-independent parameters, $J'_{awNO}$, $D_{awNO}$, $C_{alv,ss}$, $\hat{D}_{alvNO}$, $V_{aw}$, and $V_{ds}$, for one minute of tidal breathing with $q=Q_I/Q_E=t_E/t_I=2$ and $f_B=12$ min$^{-1}$.

FIG. 8 depicts 90% confidence intervals, computed for $J'_{awNO}$, $D_{awNO}$, $C_{alv,ss}$, $\hat{D}_{alvNO}$, $V_{aw}$ and $V_{ds}$, in terms of their fractional uncertainties, $\Delta x_j$, after one minute of tidal breathing with $q=2$ and $f_B=12$ min$^{-1}$. These results suggest that $J'_{awNO}$, $C_{alv,ss}$, $V_{aw}$ and $V_{ds}$ are easily estimated, since their theoretical uncertainties are less than 10% after one minute. However, $D_{awNO}$ and $\hat{D}_{alvNO}$ are more difficult to determine (their uncertainties exceed 30% after one minute).

Note that $\Delta x_j$ decreases with increasing values of $J'_{awNO}$, $D_{awNO}$, $C_{alv,ss}$, $V_{aw}$ and $V_{ds}$ (FIG. 8). However, for each of these parameters the absolute value $\Delta X_j = X_{j,0} \Delta x_j$ is nearly constant (see the graph of FIG. 8). In contrast, FIG. 8 suggests that the uncertainty of $\hat{D}_{alvNO}$, increases as its central value increases, with the confidence interval at its upper limit ($\hat{D}_{alvNO}=1.0$ s$^{-1}$) exceeding the mean by more than 500-fold. The uncertainties of $J'_{awNO}$, $D_{awNO}$, $C_{alv,ss}$, $V_{aw}$ and $V_{ds}$ are all approximately symmetric about their central values. In contrast, $\hat{D}_{alvNO}$, exhibits non-linear behavior, as evidenced by its highly skewed distributions.

Figure 9A:
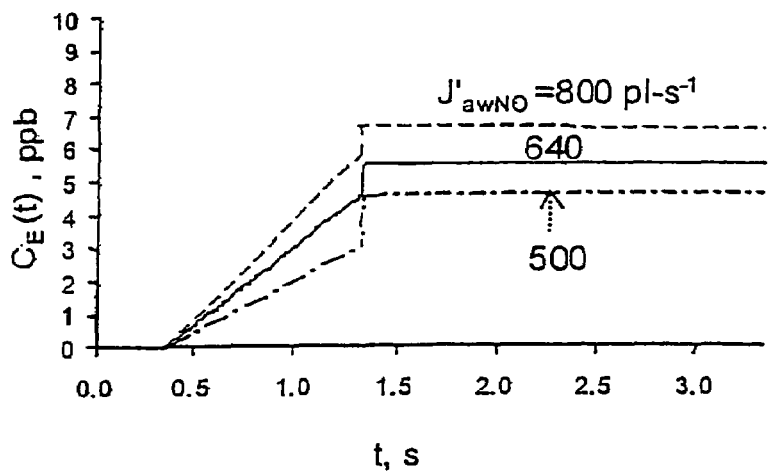
FIGS. 9A-9F are graphs showing the influence of each of the flow-independent parameters, respectively, upon the exhalation profile, $C_E(t)$, for a single tidal breath with $q=:Q_I/Q_E=t_E/t_I=2$ and $f_B=12$ min$^{-1}$ in accordance with FIGS. 7 and 8.
Figure 9B:
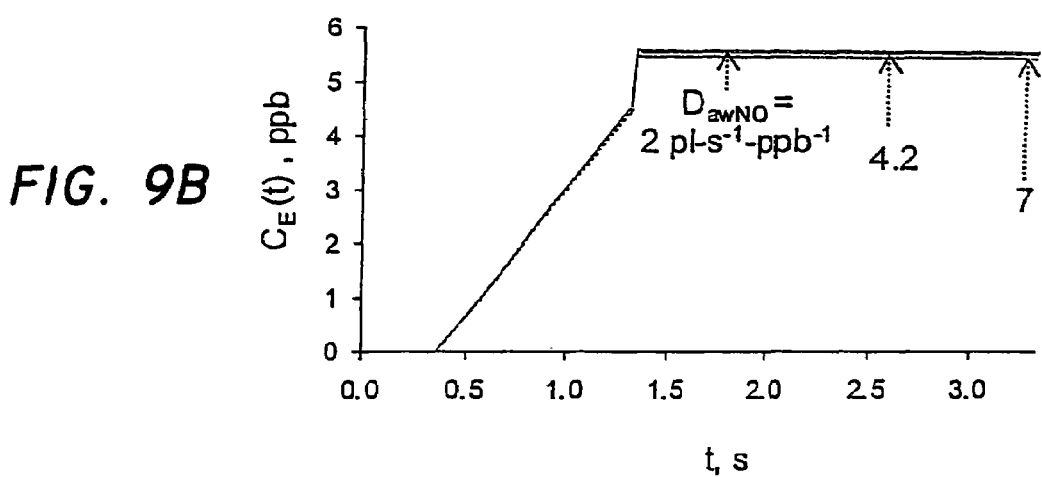
Figure 9C:
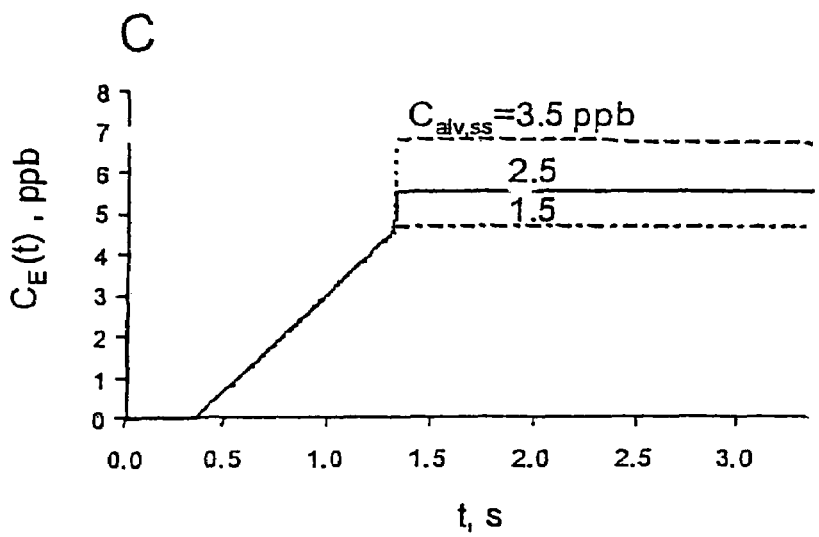
Figure 9D:
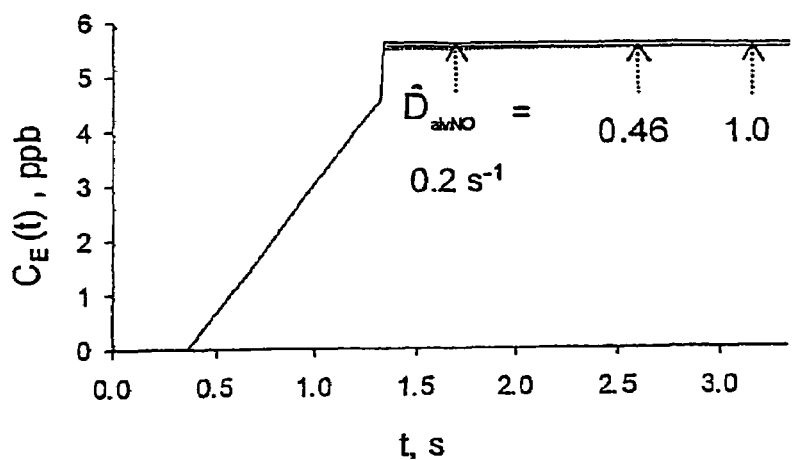
Figure 9E:
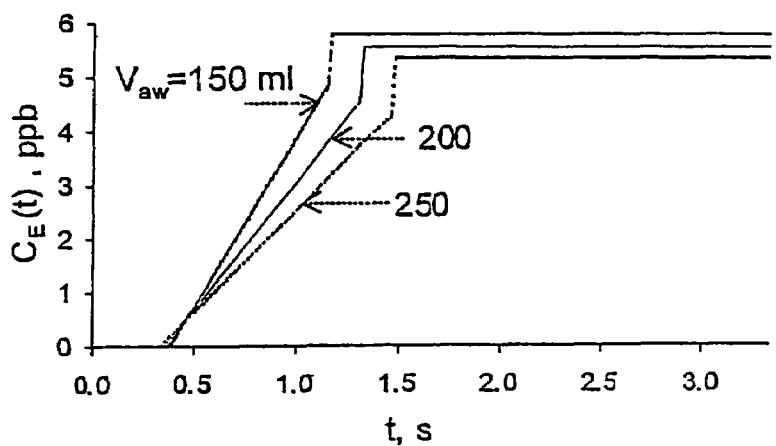
Figure 9F:
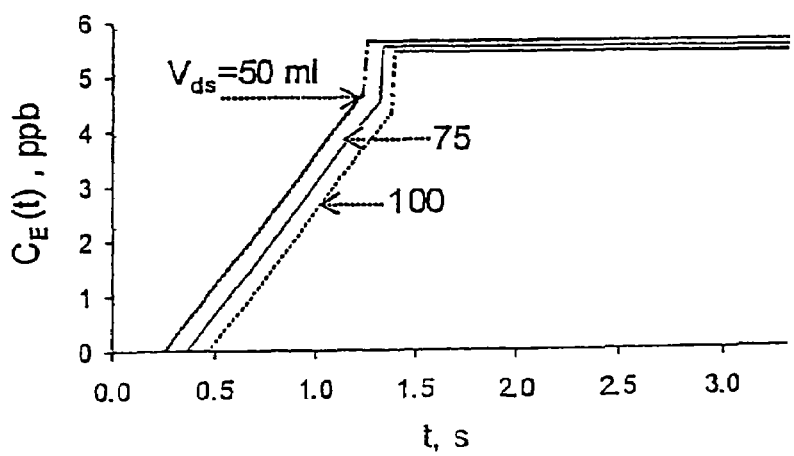

FIGS. 9A-9F illustrate the effect of variation in each flow-independent parameter upon the exhalation profile, $C_E(t)$, for a single tidal breath. Variation in $J'_{awNO}$, $C_{alv,ss}$, $V_{aw}$ and $V_{ds}$ result in significantly different exhalation profiles (FIGS. 9A, 9C, 9E and 9F). As $J'_{awNO}$ increases, $C_E(t)$ increases in both Phases II and III (FIG. 9A), whereas the effect of increasing $C_{alv,ss}$ is to increase $C_E(t)$ in Phase III alone (FIG. 9C). As shown in FIGS. 9F and 9E, the primary effects of increasing $V_{ds}$, and $V_{aw}$ are to delay the onset of Phase II and Phase III, respectively. Variation in $D_{awNO}$ and $\hat{D}_{alvNO}$ have relatively little impact upon $C_E(t)$ (FIGS. 9B and 9D, respectively). We omitted $J'_{awNO}$, $V_{aw}$ and $V_{ds}$ from subsequent analysis, and studied $D_{awNO}$ and $\hat{D}_{alvNO}$ in more detail. We also retained $C_{alv,ss}$ for comparison purposes.

Effect of the Number of Observed Tidal Breaths

Figure 10:
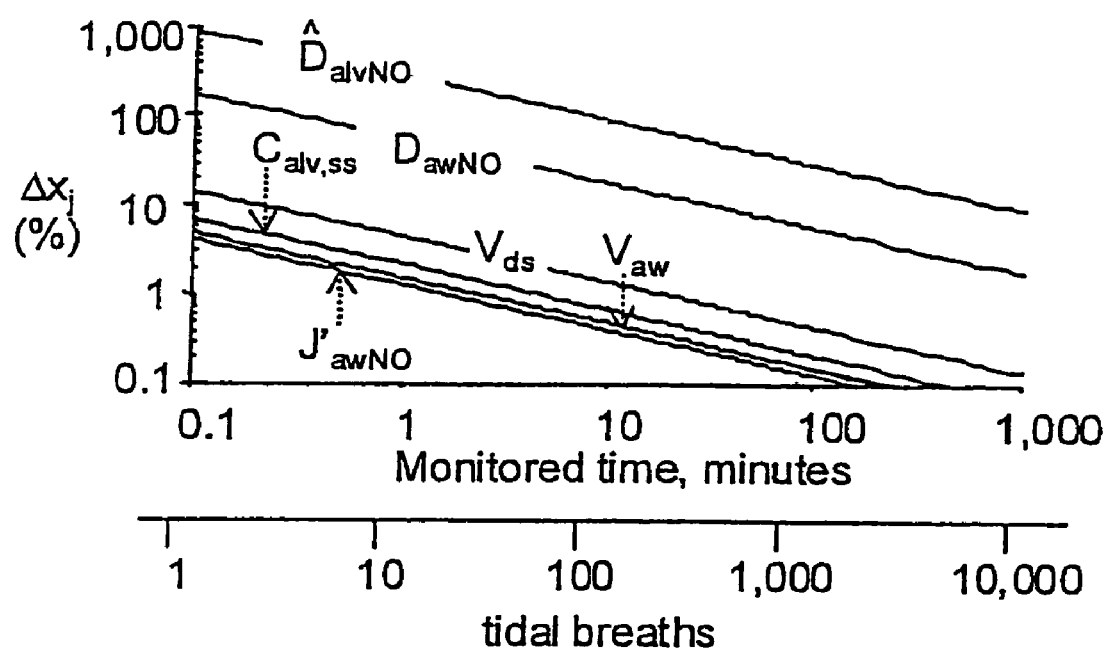
FIG. 10 is a graph showing dependence of the fractional uncertainties, $\Delta x_j$, upon total monitoring time with all flow-independent parameters at their central values, and $q=Q_I/Q_E=t_E/t_I=2$ and $f_B=12$ min$^{-1}$.

FIG. 10 shows the dependence of $\Delta x_j$ upon total monitoring time for each flow-independent parameter. In this analysis, we fixed all flow-independent parameters at their central values, with the control variables, q and $f_B$, fixed at 2 and 12 min$^{-1}$, respectively. FIG. 10 demonstrates that parameter estimates can be improved by observing more tidal breaths. After one minute, the uncertainty of $D_{awNO}$ exceeds 50%, but it is reduced to approximately 17% after ten minutes. Similarly, the uncertainty of $C_{alv,ss}$ falls from approximately 2% after one minute to below 0.7% and 0.5% after 10 and 20 minutes, respectively, and for $\hat{D}_{alvNO}$ from approximately 300% to 100% and 30%, respectively. This approach is readily implemented in practice, since tidal breathing is simple to perform. Each of the curves shown in FIG. 10 is approximately linear on a logarithmic scale, with slope ~−0.5. Thus, if $\Delta x_j$ is known after one minute, its value after 10 minutes can be estimated by dividing by the square root of 10.

Effect of Breathing Pattern

Figure 11A:
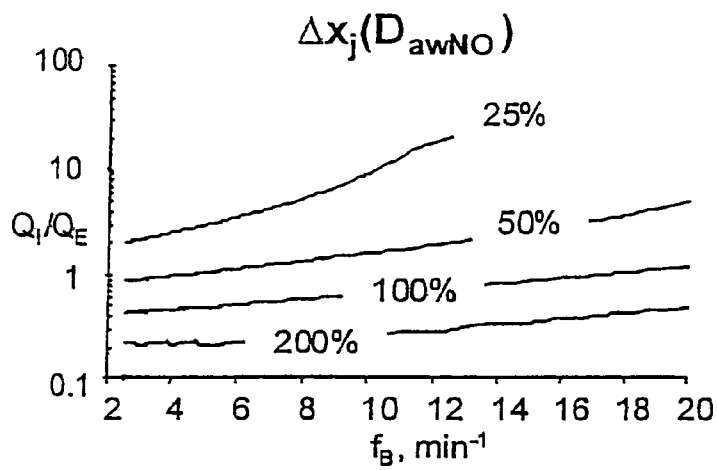
FIGS. 11A-11C are graphs showing dependence of the fractional uncertainties, $\Delta x_j$, upon the flow rate ratio, $q=Q_I/Q_E=t_E/t_I$, and breathing frequency, $f_B$(min$^{-1}$) for the flow-independent parameters $D_{awNO}$, $C_{alv,ss}$, and $\hat{D}_{alvNO}$ at their central values.
Figure 11B:
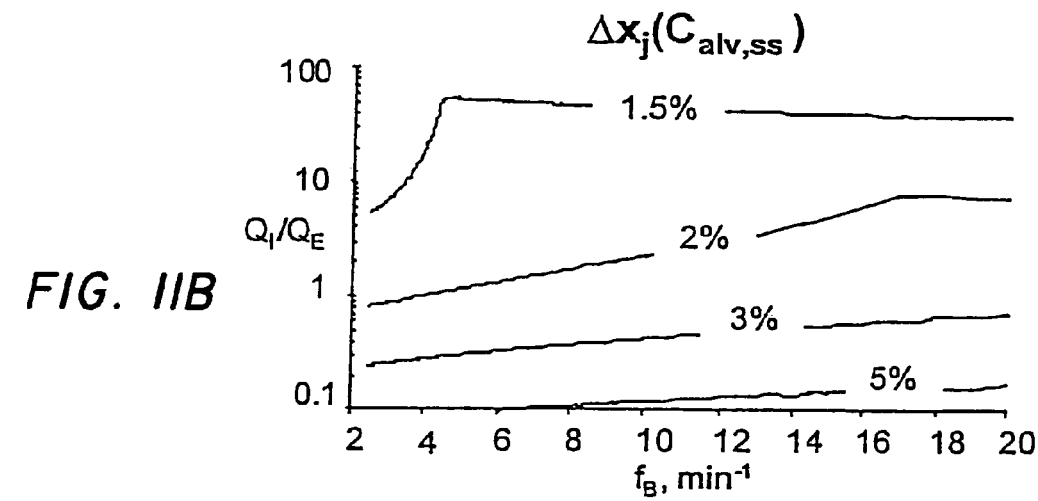
Figure 11C:
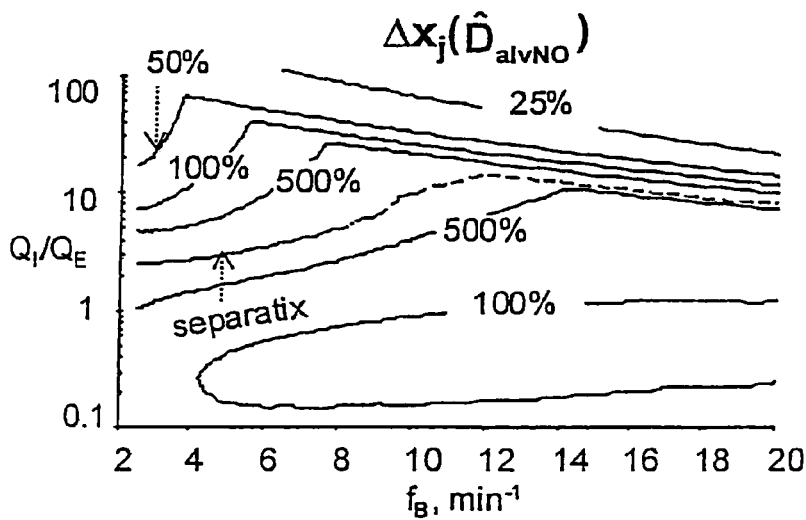

FIGS. 11A, 11B and 11C show the dependence of $\Delta x_j$ upon breathing pattern (characterized by varying the control variables, q and $f_B$) for $D_{awNO}$, $C_{alv,ss}$ and $\hat{D}_{alvNO}$, respectively. We computed these results for one minute of tidal breathing with all flow-independent parameters fixed at their central values. Low $f_B$ and high q (relatively rapid inhalation followed by very slow, sustained exhalation) favors the accurate determination $D_{awNO}$ and $C_{alv,ss}$. For one minute of tidal breathing, the uncertainty of $D_{awNO}$ is reduced below 25% for $f_B < 6$ breaths/min. and $q > 4$ (see FIG. 11A). After one minute, the uncertainty of $C_{alv,ss}$ is below 5% for nearly all physiologically relevant breathing patterns (see FIG. 11B).

The dependence of $\Delta x_j$ upon breathing pattern for $\hat{D}_{alvNO}$ is considerably more complex (see FIG. 11C). For an intermediate range of flow rate ratios, dependent on $f_B$ (e.g., approximately $2<q<10$, for $f_B>4$ breaths/min), the uncertainty of $\hat{D}_{alvNO}$ is very large. In fact, a "separatix" defines the boundary for $\hat{D}_{alvNO}$ at which $\Delta x_j \to \infty$. Furthermore, for example, after one minute with $f_B=12$ breaths/min, we may achieve $\Delta x_j<100\%$ for $\hat{D}_{alvNO}$ within two regions: $q>20$ and $1>q>0.2$. If we reduce $f_B$ to 6 breaths/min, we achieve $\Delta x_j<100\%$, for $q>40$ and $0.5>q>0.2$ (see FIG. 11C). Thus, in general, $\hat{D}_{alvNO}$ is the most difficult parameter to estimate.

Discussion

We have utilized the two-compartment model to simulate NO gas exchange in tidal breathing, and assessed the estimation of flow-independent parameters. Our analysis suggests that $J'_{awNO}$, $C_{alv,ss}$, $V_{aw}$ and $V_{ds}$, are easily characterized, whereas $D_{awNO}$ and $\hat{D}_{alvNO}$ are more difficult to determine (see FIGS. 8, 9, and 10). This is a consequence of the relatively low sensitivity of $C_E(t)$ to $D_{awNO}$ and $\hat{D}_{alvNO}$ as compared to its sensitivity to $J'_{awNO}$, $C_{alv,ss}$, $V_{aw}$ and $V_{ds}$, (see FIG. 9).

FIGS. 11A and 11B suggest that accurate determination of $D_{awNO}$ and $\hat{D}_{alvNO}$ are favored by relatively short duration inhalations ($t_I=1$ to 5 sec) followed by slow, long duration exhalations ($t_E=6$ to 12 sec). In addition, estimation of $\hat{D}_{alvNO}$ is also favored at higher breathing frequency with either slower inhalation or very rapid inhalation and very slow exhalation. Small values of $\Delta V_{alv}$ minimize the impact of systematic errors on estimates of $\hat{D}_{alvNO}$. Theoretically, breathing patterns, where $f_B<4$ breaths/min and $q>10$, are favorable to estimate both $D_{awNO}$ and $\hat{D}_{alvNO}$. However, this corresponds to $t_I<1.4$ sec, $t_E>1$ sec. and a high tidal volume change ($\Delta V_{alv} \sim 1,500$ ml), which may be difficult to achieve in practice. Furthermore, such a high tidal volume change would also result in a large systematic error ($\sim 22\%$) for $\hat{D}_{alvNO}$; which is not accounted for in this analysis. The remaining parameters, $J'_{awNO}$, $C_{alv,ss}$, $V_{aw}$, and $V_{ds}$, are readily estimated for any breathing pattern.

For identical breaths, the exhalation profile for the two-compartment model, $C_E(t)$, is predicted by Equations 3 to 5. During Phase I (Equation 3), $C_E(t)=0$, and the dead space volume, $V_{ds}$, constrains the duration of Phase I. However, Phase I does not provide any information for estimation of the other flow-independent parameters. During Phase II (Equation 4), $C_E(t)$ is independent of $C_{alv,ss}$ and $\hat{D}_{alvNO}$, but does provide information for determination of $J'_{awNO}$ and $D_{awNO}$. In addition, the duration of Phase II is constrained by $V_{aw}$. Thus, $V_{ds}$ and $V_{aw}$ are determined primarily by the relative lengths of the Phase I and Phase II time intervals. During Phase III (Equation 5), $C_E(t)$ depends upon all of the flow-independent parameters, and usually exhibits its maximum sensitivity to $J'_{awNO}$, $C_{alv,ss}$, $D_{awNO}$ and $\hat{D}_{alvNO}$ (see FIG. 9).

For single-breath maneuvers, such as pre-expiratory breathhold, Phase II plays a major role in determining $D_{awNO}$ and $J'_{awNO}$. Accumulation of NO in the airway during breathhold leads to a marked peak of NO, which is observed in expired breath during Phase II. However, for tidal breathing a single breath is completed within a much shorter time interval. Hence, much lower levels of NO accumulate in the airway compartment prior to exhalation, and, in most cases, an NO peak is not observed during Phase II.

An element of air appearing in expired breath during Phase II, existed within the airway compartment, at some position $V<V_{aw}$, at the start of exhalation. Thus, its residence time in the airway compartment is: $(V_{aw}-V)/Q_E<\tau_{Ea}=V_{aw}/Q_E$. However, an air element, which appears in expired breath during Phase III, originated within the alveolar compartment, and its residence time in the airway compartment is $\tau_{Ea}$. Thus, the residence time of expired air is longer in Phase III than in Phase II, which results in greater sensitivity of $C_E(t)$ to the airway parameters, $D_{awNO}$ and $J'_{awNO}$, on the Phase III time intervals. Therefore, for fixed monitoring time, optimal estimates for $D_{awNO}$, $J'_{awNO}$, $C_{alv,ss}$ and $\hat{D}_{alvNO}$, are determined by maximizing the Phase III exhalation interval for tidal breathing (i.e., short duration inspiration with longer duration expiration as described previously), since the sensitivity of $C_E(t)$ to all of these parameters is maximum on this interval.

FIGS. 11A and 11B show that $\Delta x_j$ decreases with increasing $q=Q_I/Q_E=t_E/t_I$ and decreasing $f_B$ for $D_{awNO}$ and $C_{alv,ss}$, which implies that $\Delta x_j$ decreases as $t_E$ and $Q_I$ increase, and as $Q_E$ decreases. Therefore, short duration inhalation at high flow followed by long duration inhalation at low flow facilitates estimation of these parameters. Long exhalation times at low flow allow higher NO concentrations to accumulate in the airway. Higher airway concentration increases the exhalation profile's sensitivity to $D_{awNO}$. Thus, the uncertainty of $D_{awNO}$ is minimized under these conditions.

Short inhalation times at high flow transport less NO into the alveolar compartment from the airway compartment, which leads to enhanced sensitivity of the Phase III exhalation profile to $C_{alv,ss}$. In addition, greater $\Delta V_{alv}$ allows significant amounts of air from the alveolar compartment to reach the mouth, further increasing the sensitivity of the Phase III exhalation profile to $C_{alv,ss}$. At constant alveolar ventilation rate (specified herein as $\dot{V}_{alv}=5,000$ ml/min), $\Delta V_{alv}$ is inversely proportional to $f_B$. Therefore, lower breathing frequencies result in improved estimates for $C_{alv,ss}$.

At very low breathing frequencies ($f_B<5$ breaths/min, see FIG. 11C), similar dynamics result in conditions favorable to estimates of $\hat{D}_{alvNO}$. Long exhalation times at low flow build up an appreciable amount of NO in the airway, which is transported into the alveolar region on a subsequent (rapid) inhalation. Unfortunately, such low breathing frequencies are difficult to achieve in practice. However, at slightly higher breathing frequencies ($5<f_B<8$ breaths/min), the uncertainty of $\hat{D}_{alvNO}$ decreases with increasing $f_B$, and is minimized in two distinct regions at very high or low values of $q$. For example, with $f_B=12$ breaths/min, we achieve $\Delta x_j<100\%$, for $q>20$ and $1>q>0.2$ (see FIG. 11C). Under these conditions $\hat{D}_{alvNO}$ becomes very sensitive to the concentration difference, $(C_{alv,I}-C_{alv,ss})$, and we can approximate $\Delta x_j$ as inversely proportional to the absolute value, $|C_{alv,I}-C_{alv,ss}|$.

For $q<1$, the time duration of inhalation exceeds that for exhalation ($t_I>t_E$), and more of the NO accumulated in the airway is transported into the alveolar region during inhalation than is removed during exhalation. Thus, $C_{alv,I}>C_{alv,ss}$, which provides a gradient for NO transport from airspace to tissue in the alveolar compartment, and increases the sensitivity of $C_E(t)$ to $\hat{D}_{alvNO}$. Thus, at any fixed breathing frequency, we can determine a critical flow rate ratio, where $|C_{alv,I}-C_{alv,ss}|$ is maximized (e.g., $q \sim 0.5$ for $f_B=12$ breaths/min, see FIG. 11C). As $q$ increases, a second critical flow rate ratio is reached where $C_{alv,I}=C_{alv,ss}$, and $\hat{D}_{alvNO}$ cannot be determined ($q \sim 15$ for $f_B=12$ breaths/min, see FIG. 11C). As $q$ increases further, $C_{alv,I}<C_{alv,ss}$, and $|C_{alv,I}-C_{alv,ss}|$ increases. Thus, less of the NO accumulated in the airway is transported into the alveolar region during inhalation than is removed during exhalation. This effect again provides a gradient for NO transport from tissue to airspace in the alveolar compartment, which increases the sensitivity of $C_E(t)$ to $\hat{D}_{alvNO}$. Therefore, improved estimates of $\hat{D}_{alvNO}$ are favored when $C_{alv}(t)$ becomes more dependent upon its history and significantly deviates from $C_{alv,ss}$. Furthermore, these results suggest that estimates of $\hat{D}_{alvNO}$ should be strongly dependent upon $C_{alv,ss}$.

We have not addressed the potential impact of systematic errors upon parameter estimates from experimental data, such as the dependence of $\hat{D}_{alvNO}$ upon $V_{alv}$. Large tidal volume changes may adversely affect estimation of $\hat{D}_{alvNO}$, since increasing $\Delta V_{alv}/V_{alv}$ results in greater variation of $\hat{D}_{alvNO}$ over the time course of exhalation. Additional systematic errors may be introduced by the finite response time of the analytical monitoring system. Time lags, resulting from such limitations as finite instrument response time, transit times in instrument plumbing, etc., are negligible for single breath maneuvers. However, time lags are more important for tidal breathing, due to the shorter time duration of each breath. Imprecise modeling of time lags may result in miss-alignment of experimental concentration and flow rate profiles, thereby causing incorrect placement of the Phase I, II and III time windows. Thus, precise characterization of system time lags is necessary to facilitate accurate parameter estimates from tidal breathing data. These time lags are dependent upon $V_{aw}$ and $V_{ds}$, which have not been estimated from experimental data in previous efforts. Fortunately, the results presented herein suggest that $V_{ds}$ and $V_{aw}$ are readily determined from experimental data, since these two parameters depend upon the time durations of the Phase I and Phase II intervals, respectively.

Conclusions

Our results are based on the central values of the flow-independent parameters, shown in the table of FIG. 7. If the flow-independent parameters deviate significantly from their central values, appropriate modifications to this protocol are readily determined using the methodology presented. Our analysis suggests that $J'_{awNO}$, $C_{alv,ss}$, $V_{ds}$, and $V_{aw}$ should be readily determined from tidal breathing; however, $D_{awNO}$ and $D_{alvNO}$ are more difficult to estimate, and may require multiple tidal breathing patterns, or a relatively large number of tidal breaths. In addition, a short inspiration time relative to expiration reduces the uncertainty for all of the flow-independent parameters. We conclude that a tidal breathing pattern has the potential to characterize flow-independent NO exchange parameters.

Nomenclature and Abbreviations $C_{air}=C_{air}(t,V)$=NO concentration in the airway gas space (ppb).

$C_{air,end}=C_{air}(t,V=0)$ for inhalation, and $C_{air,end}=C_{alv}$ for exhalation (ppb).

$C_{alv}(t)$=gas phase NO concentration in alveolar compartment (ppb).

$C_{alv,0}=C_{alv,E}=C_{alv}(t=0)$=final (exhalation) alveolar concentration at t=0 (ppb).

$C_{alv,I}=C_{alv}(t=t_I)$=final (inhalation) alveolar concentration at $t=t_I$ (ppb).

$C_{alv,ss}$=steady state alveolar concentration (ppb).

$C_{awNO}=J'_{awNO}/D_{awNO}$=equivalent gas phase, airway tissue concentration (ppb).

$C_D(t)$ $C_D(nT_s)$=observed (experimental) NO exhalation profile (signal) (ppb).

$C_E(t)$ NO concentration at mouth (exhalation profile) (ppb).

$D_{alvNO}$=diffusing capacity of NO in the alveolar region (ml/s).

$\hat{D}_{alvNO}=D_{alvNO}/V_{alv}$=alveolar diffusing capacity per unit alveolar-volume ($s^{-1}$).

$D_{awNO}$=airway diffusing capacity (ml-$s^{-1}$-$ppb^{-1}$ or pl-$s^{-1}$-$ppb^{-1}$).

$\hat{D}_{awNO}=D_{awNO}/V_{aw}$.

$f_a=f_{a1}+f_{a2}$.

$f_{a1}=[1-e^{-D_{awNO}t_I(\tau_{Ea}+\tau_{Ia})-D_{alvNO}(t_I-\tau_{Ia}-\tau_{Ids})}]/\hat{D}_{alvNO}$.

$f_{a2}=\hat{D}_{awNO}(1+q)[e^{-D_{alvNO}t_I}-e^{-D_{awNO}t_I(\tau_{Ea}+\tau_{Ia})-D_{alvNO}(t_I-\tau_{Ia})}]/[\hat{D}_{alvNO}(\hat{D}_{alvNO}-\hat{D}_{awNO})(1+q)]$.

$f_B=q/[(I+qt_E)]$=breathing frequency.

$f_t=f_{a1}+f_{a2}+[e^{-D_{awNO}\tau_{Ia}-D_{alvNO}(t_I-\tau_{Ids}-\tau_{Ia})}-e^{-D_{awNO}\tau_{Ia}}]/\hat{D}_{alvNO}$.

$f_{QI}=f_{QI1}+f_{QI2}-f_{QI3}$.

$f_{QI1}=e^{-D_{awNO}(\tau_{Ea}+\tau_{Ia})-D_{alvNO}(t_E+t_I-\tau_{Eds}-\tau_{Ea}-\tau_{Ia})}/[(1+q)\hat{D}_{alv}]$.

$f_{QI2}=e^{-D_{awNO}(\tau_{Ea}+\tau_{Ia})-D_{alvNO}(t_E+t_I-\tau_{Ea}-\tau_{Ia})}/[(1+q)\hat{D}_{alvNO}(\hat{D}_{alvNO}-\hat{D}_{awNO})]$.

$f_{QI3}=e^{-D_{alvNO}(t_I+t_E)}/[(1+q)(\hat{D}_{alvNO}-\hat{D}_{awNO})]$.

FRC, functional reserve capacity.

j=index for flow-independent parameters (j=1, ..., P=6).

$J'_{alvNO}$=global maximum flux of NO in alveolar compartment (ml-ppb/s).

($J'_{alvNO}$ is defined as the flux of NO into the alveolar compartment, if $C_{alv}(t)=0$).

$J_{awNO}$=net flux of NO into the air space of the airway compartment (pl/s or ml/s).

$J_{awNO}=J'_{awNO}-D_{awNO}C=D_{awNO}[C_{awNO}-C]$.

$J'_{awNO}$=maximum volumetric airway flux (pl/s or ml/s).

$J_{alvNO}$=net flux of NO into the air space of the alveolar compartment (ml-ppb/s).

$J_{alvNO}=J'_{alvNO}-D_{alvNO}C_{alv}(t)=D_{alvNO}[C_{alv,ss}-C_{alv}(t)]$.

L=Summation from m=1 to M of $N_m$=total number of exhalation profile measurements in M breaths.

m=index for tidal breaths, m=1, 2, ... M.

M=total number of tidal breaths observed in an exhalation profile sequence.

n=index for data samples=$(t-t_I)/T_s$, n=0, 1, 2, ... $N_m$; in tidal breath, m.

$N_m$=number of sampled concentrations in tidal breath, m.

pl, picoliter.

$P_m=Q_{E,m}/Q_{E,m-1}$ ppb, parts per billion.

P=Number of fitted flow-independent parameters (P=6).

$q=Q_I/Q_E=t_E/t_I$=flow rate ratio.

$q_1=(Q_I/Q_E)_1=(t_E/t_I)_1$, flow rate ratio for the first observed breath (m=1).

$q_m=(Q_I/Q_E)_m=(t_E/t_I)_m$, flow rate ratio for breath, m.

Q=volumetric, air flow rate=$-Q_I$ (inhalation), $Q_E$ (exhalation) (ml/s).

$Q_E$=air flow rate averaged over exhalation time interval (ml/s).

$Q_{E,m}$=average exhalation air flow rate for breath, m (ml/s).

$Q_I$=air flow rate averaged over inhalation time interval (ml/s).

$Q_{I,m}$=average inhalation air flow rate for breath, m (ml/s).

rms, root-mean-squared.

$S_{i,j}$=sensitivity of an output, i, to an input, j.

$S^r_{i,j}$=normalized or relative sensitivity of an output, i, to an input, j.

$S^{sr}_{i,j}$=semi-relative sensitivity of an output, i, to an input, j.

$|\overline{S}^{sr,rm}\hat{D}_{alvNO}{}^s c_i j|$=time-averaged (rms) semi-relative sensitivity of $Y_i$ to $X_j$.

t=time (s).

$t_E$ exhalation time interval (s).

$t_I$ inhalation time interval (s).

Ts=sampling time of observed concentration data=0.02 s (50 Hz).

V=axial position in units of cumulative volume (ml).

$V_{alv}(t)$=alveolar compartment volume (ml).

$V_{alv,E}=V_{alv}(t=0)=\{V_{alv}(t=t_I+t_E)= \ldots$ for identical breaths$\}$ (ml).

$V_{alv,I}=V_{alv}(t=t_I)=\{V_{alv}(t=2t_I+t_E)= \ldots$ for identical breaths$\}$ (ml).

$V_{aw}$=airway compartment volume (ml).

$V_{ds}$=dead space compartment volume (ml).

$X_j$=variation in flow-independent parameter, j, around its fitted value, $X_{j,0}$.

$X_{j,0}$=best unbiased estimate fitted value of flow-independent parameter, j.

$Y(n)=[C_E(n)-C_D(n)]$=discrete time experimental measurement error (ppb).

$Y(t)=[C_E(t)-C_D(t)]$=experimental measurement error (ppb).

$\Delta V_{alv,max}=[V_{alv,I}-V_{alv,0}]_{max}$=maximum tidal volume change (ml).

$\Delta V_{alv}$=tidal volume change (ml).

$\Delta x_j$=fractional uncertainty of flow-independent parameter, j.

$\Delta X_j$=uncertainty of flow-independent parameter, j.

$\tau_E=V/Q_E$=exhalation residence time (s).

$\tau_{Ea}=V_{aw}/Q_E$=exhalation residence time for the airway compartment (s).

$\tau_{Eds}=V_{ds}/Q_E$=exhalation residence time for the dead space compartment (s).

$\tau_I=V/Q_I$=inhalation residence time (s).

$\tau_{Ia}=V_{aw}/Q_I$=inhalation residence time for the airway compartment (s).

$\tau_{Ids}=V_{ds}/Q_I$=inhalation residence time for the dead space compartment (s).

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A method of determining which flow-independent parameters of nitric oxide exchange in the lungs are characterized within an interval of acceptable accuracy during tidal breathing, comprising:

having a subject perform a tidal breathing maneuver; measuring and recording NO concentration and flow rate simultaneously during the maneuver;

simulating the tidal breathing maneuver by a two-compartment model;

fitting recorded subject flow rate and exhaled NO concentration to results obtained from the simulating of the tidal breathing maneuver from the two-compartment model; and comparing in a processing or electronic device the recorded subject flow rate and exhaled NO concentration and the results obtained from the simulating of the tidal breathing maneuver to diagnose respiratory disease.

2. The method of claim 1, further comprising:

filtering the measured data; and providing the measured data as a time dependent flow profile.

3. The method of claim 1, wherein the step of comparing further comprises identifying three to six of the flow-independent parameters of NO exchange that can be accurately characterized by the two-compartment model.

4. The method of claim 1, wherein the step of comparing further comprises computing a 90% confidence interval for each of the flow-independent parameters after one minute of the tidal breathing; observing which of the flow-independent parameters are within a 10% uncertainty interval;
   observing skewing about respective central values of the flow-independent parameters; and
   identifying the flow-independent parameters that can be estimated within a 10% interval of the central value after one minute.

5. The method of determining of claim 4, wherein:
   the step of computing comprises computing a 90% confidence interval for the flow independent parameters including $J'_{awNO}$, $D_{awNo}$, $C_{alv,ss}$, $\hat{D}_{alvNO}$, $V_{aw}$ and $V_{da}$; and
   the step of identifying further comprises identifying $J'_{awNO}$, $C_{alv,ss}$, $V_{aw}$ and $V_{da}$.

6. The method of determining of claim 4, further comprising: observing an effect of increasing a monitoring time of tidal breathing on the accuracy of estimating the parameters.

7. The method of determining of claim 4, further comprising: varying the breathing pattern during a monitoring time of the tidal breathing and observing an effect of said varying on the accuracy of estimating the parameters.

8. A method of diagnosing a respiratory disease by utilizing data gathered during tidal breathing, comprising:
   having a subject perform a tidal breathing maneuver;
   measuring and recording NO concentration and flow rate simultaneously during the maneuver;
   simulating the tidal breathing maneuver by a two-compartment model;
   fitting recorded subject flow rate and exhaled NO concentration to results obtained from the simulating of the tidal breathing maneuver from the two-compartment model; and
   comparing in a pg or electronic device the recorded subject flow rate and exhaled NO concentration and the results obtained from the simulating of the tidal breathing maneuver to diagnose a respiratory disease.

9. The method of diagnosing a respiratory disease of claim 8, wherein the step of fitting further comprising:
   filtering the measured data; and
   performing a least squares fit of the measured data relative to the simulated data.

10. The method of diagnosing of claim 8, wherein:
    the step of measuring further comprises measuring and recording said concentration and flow rate over a monitoring time;
    the step of simulating further comprises forming a flow rate and concentration profile of estimated time dependent values; and
    wherein the step of comparing further comprises comparing the measured concentrations to corresponding estimated values from the flow rate and concentration profile.

11. The method of diagnosing of claim 10, further comprising evaluating the significance of differences between selected flow-independent parameters in the measured concentration and the estimated values of the concentration profile.

* * * * *